United States Patent [19]
James et al.

[11] Patent Number: 5,770,144
[45] Date of Patent: Jun. 23, 1998

[54] METHOD OF FORMING IMPROVED APERTURED FILMS BY USING FLUID PERFORATION

[75] Inventors: William A. James, Pennington; William G. F. Kelly, Middlesex; Charles James Shimalla, Plainsboro, all of N.J.

[73] Assignee: McNeil-PPC, Inc., New Brunswick, N.J.

[21] Appl. No.: 523,112

[22] Filed: Sep. 1, 1995

[51] Int. Cl.$^6$ .................................................. B29C 59/06
[52] U.S. Cl. ...................... 264/504; 264/156; 428/131; 425/387.1; 425/290; 83/30; 83/53; 83/177
[58] Field of Search .................... 264/504, 156; 428/131; 425/387.1, 290; 83/30, 53, 177

[56] References Cited

U.S. PATENT DOCUMENTS

| | | | |
|---|---|---|---|
| 3,632,269 | 1/1972 | Doviak et al. | 264/154 |
| 3,746,607 | 7/1973 | Harmon et al. | 428/167 |
| 3,929,135 | 12/1975 | Thompson | 128/287 |
| 4,324,246 | 4/1982 | Mullane et al. | 128/287 |
| 4,342,314 | 8/1982 | Radel et al. | 128/287 |
| 4,351,784 | 9/1982 | Thomas et al. | 264/22 |
| 4,381,326 | 4/1983 | Kelly | 264/22 |
| 4,456,570 | 6/1984 | Thomas et al. | 428/171 |
| 4,535,020 | 8/1985 | Thomas et al. | 264/504 |
| 4,609,518 | 9/1986 | Curro et al. | 604/383 |
| 4,637,819 | 1/1987 | Ouellette et al. | 604/369 |
| 4,690,679 | 9/1987 | Mattingly, III et al. | 428/134 |
| 4,695,422 | 9/1987 | Curro et al. | 264/504 |
| 4,839,216 | 6/1989 | Curro et al. | 604/385.1 |
| 4,867,881 | 9/1989 | Kinzer | 210/490 |
| 4,950,264 | 8/1990 | Osborn, III | 604/385.1 |
| 5,009,653 | 4/1991 | Osborn, III | 428/131 |
| 5,112,690 | 5/1992 | Cohen et al. | 428/411.1 |
| 5,342,334 | 8/1994 | Thompson | 604/366 |
| 5,352,217 | 10/1994 | Curro | 604/378 |
| 5,368,910 | 11/1994 | Langdon | 428/137 |
| 5,368,926 | 11/1994 | Thompson et al. | 428/284 |
| 5,376,439 | 12/1994 | Hodgson et al. | 428/220 |
| 5,382,245 | 1/1995 | Thompson et al. | 604/367 |
| 5,382,703 | 1/1995 | Nohr et al. | 568/609 |
| 5,383,870 | 1/1995 | Takai et al. | 604/37.8 |
| 5,387,290 | 2/1995 | Yamamoto et al. | 604/384 |

FOREIGN PATENT DOCUMENTS

| | | |
|---|---|---|
| 0 432 882 A2 | 6/1991 | European Pat. Off. . |
| 0 598 204 A1 | 5/1994 | European Pat. Off. . |
| 0 626 158 A1 | 11/1994 | European Pat. Off. . |
| 0 626 159 A1 | 11/1994 | European Pat. Off. . |
| 0 304 617 B1 | 1/1995 | European Pat. Off. . |
| 0 640 328 A1 | 3/1995 | European Pat. Off. . |
| 3-286762 | 12/1991 | Japan . |
| WO 93/15701 | 2/1992 | WIPO . |
| WO 94/18926 | 2/1994 | WIPO . |
| WO 94/22408 | 3/1994 | WIPO . |
| WO 92/18078 | 4/1994 | WIPO . |
| WO 94/28846 | 6/1994 | WIPO . |
| WO 95/00093 | 6/1994 | WIPO . |

Primary Examiner—William Watkins
Attorney, Agent, or Firm—Rockey, Milnamow & Katz, Ltd.

[57] ABSTRACT

An apertured film for use as a topsheet in absorbent products wherein the film is apertured and includes a plurality of micro-holes and a plurality of large-sized holes. A method of forming the film is disclosed, as well as an absorbent product incorporating the apertured film as a topsheet. The method includes the step of supporting the starting film on a backing member which has recessed zones into which the film may be deformed. In the preferred embodiment, fluid in the form of columnar streams is directed from at least two sets of orifices against the upper surface of the starting film. The orifices of the first set have a diameter greater than 10 mils, and the orifices of the second set have a diameter less than or equal to 10 mils. The fluid is discharged from the smaller orifices at a pressure of at least 500 psig, and the fluid is discharged from the larger orifices at a pressure less than 500 psig.

24 Claims, 20 Drawing Sheets

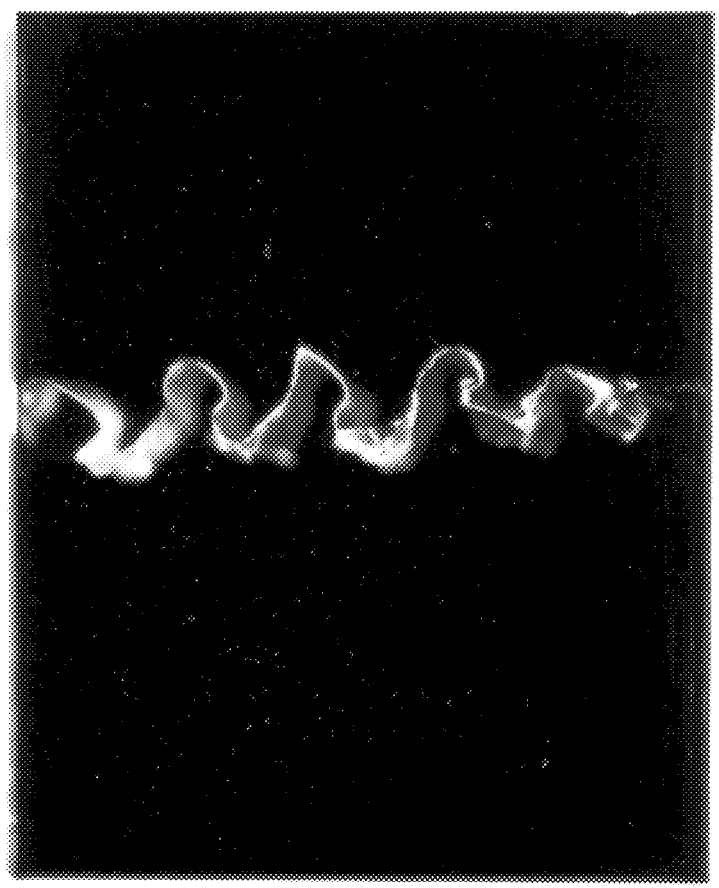
Fig. 16
Fig. 17
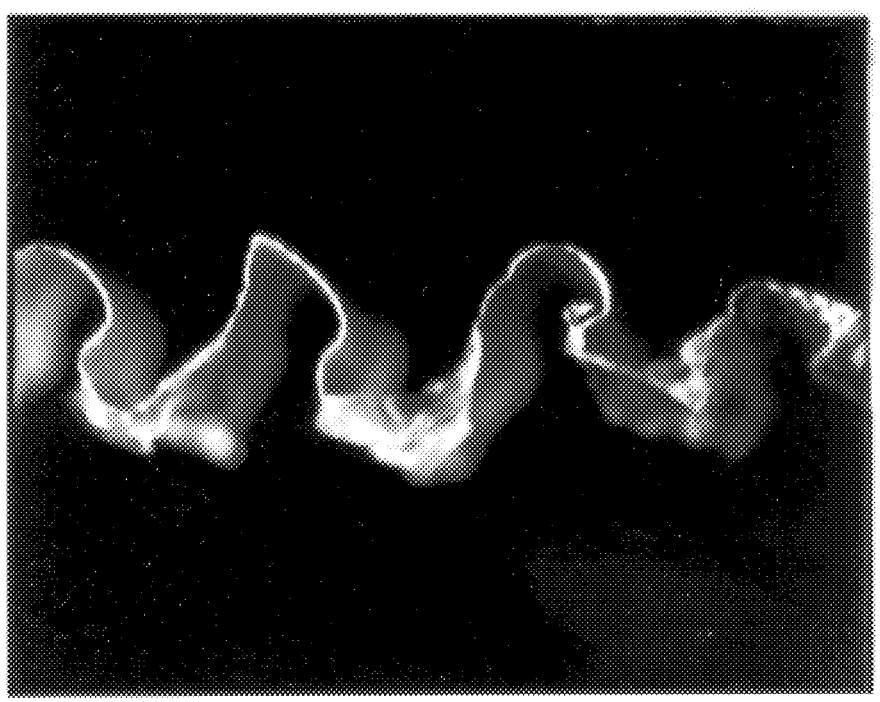

METHOD OF FORMING IMPROVED APERTURED FILMS BY USING FLUID PERFORATION

FIELD OF THE INVENTION

This invention relates to apertured films having primary utility as a cover member for an absorbent article, and to methods and apparatus for forming such apertured films.

BACKGROUND OF THE INVENTION

For many years it has been common to use nonwoven fabrics as a cover member, or facing layer, for products that are adapted to receive body discharges, such as disposable diapers, sanitary napkins, adult incontinent devices, wound dressings and the like. Such fabrics have typically been formed by air-laying, carding, spun bonding and the like, and it is known to post-treat such fabrics to provide strength and integrity, as by the application of binders or fiber entanglement, either mechanically or by the application of fluid forces. Since such fabrics are often formed of hydrophobic material, it is also known to post-treat such fabrics with surface active agents to promote the passage of body discharges through the fabric. Such fabrics have, or are perceived to have, desirable characteristics such as breathability, drapeability, softness, and pleasant hand and tactile impression.

One of the drawbacks associated with facing layers formed of a nonwoven fabric is that liquid such as urine, menses, wound exudates, and the like that passes through the facing layer and into the absorbent core has a tendency to strike back through the facing layer, particularly under pressure and when the liquid in the absorbent core approaches the volumetric storage capacity of the core. For this reason, and other reasons, it has been known in the past to utilize apertured plastic films as the facing layer in absorbent articles.

The following list includes disclosures of such apertured films in issued U.S. and foreign patents and published patent applications.
U.S. Pat. No. 3,632,269-Doviak et al.
U.S. Pat. No. 3,929,135-Thompson et al.
U.S. Pat. No. 4,324,246-Mullane
U.S. Pat. No. 4,351,784-Thomas et al.
U.S. Pat. No. 4,381,326-Kelly
U.S. Pat. No. 4,456,570-Thomas et al.
U.S. Pat. No. 4,535,020-Thomas et al.
U.S. Pat. No. 4,690,679-Mattingly et al.
U.S. Pat. No. 4,839,216-Curro et al.
U.S. Pat. No. 4,950,264-Osborn
U.S. Pat. No. 5,009,653-Osborn
U.S. Pat. No. 5,112,690-Cohen et al.
U.S. Pat. No. 5,342,334-Thompson et al.
U.S. Pat. No. 5,352,217-Curro
U.S. Pat. No. 5,368,910-Langdon
U.S. Pat. No. 5,368,926-Thompson et al.
U.S. Pat. No. 5,376,439-Hodgson et al.
U.S. Pat. No. 5,382,245-Thompson et al.
U.S. Pat. No. 5,382,703-Nohr et al.
U.S. Pat. No. 5,383,870-Takai et al.
U.S. Pat. No. 5,387,209-Yamamoto et al.
EP 0 304 617-Suda et al.
EP 0 432 882 A2-Shipley
EP 0 598 204 A1-Garavaglia et al.
EP 0 626 158 A1-Coles et al.
EP 0 626 159 A1-Taki et al.
EP 0 640 328-Tanaka et al.
JP 3-286762 A-Yamamoto et al.
WO 92/18078 A1-Colbert
WO 93/15701 A1-Turi et al.
WO 94/18926 A1-Perry
WO 94/22408 A1-Langdon
WO 94/28846 A1-Steiger et al.
WO 95/00093 A2-Osborn et al.

While certain of such apertured films have functioned reasonably well for their intended purposes, the vast majority of such films have actual and perceived major deficiencies. For example, even though such apertured films may permit fluid to readily pass therethrough, and may minimize strike-back of such fluid, such apertured films nevertheless tend to have the appearance, feel and hand of a film, rather than a fabric. Such film-like characteristics are considered as a negative by the consumer, and thus absorbent products with apertured films as a facing layer have not met with widespread consumer acceptance.

Major improvements for apertured film facing layers for absorbent products are disclosed in commonly assigned, copending U.S. patent application Ser. Nos. 08/417,404 U.S. Pat. No. 5,567,376 and 08/417,408 abandoned to Turi et al. filed Apr. 5, 1995 as a continuation and a division of Ser. No. 08/004,379 abandoned, filed Jan. 14, 1993 as a continuation of Ser. No. 07/744,744 abandoned, filed Aug. 14, 1991 (corresponding to publication WO 93/15701 A1 on the above list). In the above-mentioned Turi et al. applications, an apertured film, and methods and apparatus for forming the film, are disclosed which impart to the film physical characteristics like those of nonwoven fabrics. This is accomplished by supporting a film formed of stretchable thermoplastic polymeric material on localized support regions of a backing member, and directing a fluid in the form of high pressure, small diameter columnar jets against the upper surface of the film, so that unsupported portions of the film are directed downwardly between the support regions to cause the formation of micro-holes and fiber-like elements (fibrils) thereabout to impart to the apertured film physical characteristics of appearance, softness, feel and hand, like those of a nonwoven fabric. While such apertured films are a marked improvement over prior art apertured films, it is desired to provide further improvements in such apertured films, as by improving the ability of such films to pass viscous fluids, such as menses.

For use of apertured films as topsheets for sanitary napkins, clean-dry properties are very much desired. This means that the sanitary napkin should appear clean and dry to the user even after it has accepted a flow of menstrual fluid. There are many factors affecting the clean-dry properties of a sanitary napkin, including the aperture characteristics and open area of the napkin cover material. There is a trade-off in the effects of the film aperture size and open area on clean-dry properties. On the one hand, large apertures allow the fluid to be more rapidly transmitted to the absorbent core. On the other hand, apertures that are too large permit the fluid to be transported back through the topsheet from the absorbent core (a phenomenon sometimes referred to as "strike back") and to contact the wearer. Furthermore, large open areas tend to allow the stain on the absorbent core of the napkin to be visible through the topsheet and give the wearer the perception that the product has not kept her clean. To exhibit both clean and dry properties, a topsheet must have a carefully balanced combination of aperture size and open area: large enough apertures to rapidly accept a flow of menstrual fluid and to allow it to pass through to the napkin's absorbent core, but small enough to mask the stain on the underlying absorbent core to give the wearer the perception of cleanliness.

SUMMARY OF THE INVENTION

In accordance with one aspect of the present invention, apertured films of the type disclosed in the above-mentioned Turi et al. patent applications are improved by providing such films with larger apertures and a sufficient open area so that viscous fluids, such as menses, can flow readily through the film. These improved properties are imparted to the film by subjecting the film to fluid forces in the form of columnar streams or jets from at least two sets of orifices, the orifices of one set having a diameter greater than ten mils, and the fluid supplied to the orifices having a relatively low pressure less than about 500 psig, and the orifices of at least one other set having a diameter of less than or equal to ten mils and the fluid supplied thereto having a relatively high pressure greater than about 500 psig. The present invention can be practiced with selective variation of the sequence to which the film is subjected to fluid forces from the low and high pressure orifices, that is, first low pressure then high pressure, or first high pressure then low pressure, or other combinations or variations.

The apertures are, for the most part, irregular in shape and size. They are measured by various techniques that approximate the diameter, which may be expressed as equivalent hydraulic diameter (EHD) or equivalent circular diameter (ECD). The resulting apertured film has a combination of large sized apertures having average EHD's of from about 7 mils to about 30 mils, and small sized apertures having average EHD's of from about 1 mil to about 7 mils. Such apertured films have an open area in the range of from about 3% to about 13%.

The improved apertured film of the present invention is preferably formed on a backing member like that shown in FIGS. 17–19 of the above-mentioned Turi et al. applications, which results in the film having a series of generally parallel ridges formed by generally vertically oriented side walls which define a series of generally parallel valleys. The film thus includes generally parallel alternating solid or closed portions of the film separated by apertured or open portions of the film, that contain the aforementioned combination of large and small sized apertures. Both size apertures are formed as a result of elongating and drawing the stretchable material between the localized support regions of the backing member as a result of the application of fluid pressure, and as the film elongates it undergoes thinning until it finally reaches the point of rupturing (i.e., splitting and fibrillating) to form the above-mentioned apertures.

As with apertured films disclosed in the Turi et al. applications, the apertures are surrounded by a network of fiber-like elements or micro-strips of drawn plastic material. Such drawn fiber-like elements (fibrils) cooperate with the apertures to provide the apertured film with physical characteristics similar to those of nonwoven fabrics. The fiber like elements have lengths varying from about 0.005 inch (0.013 cm) to about 0.05 inch (0.127 cm), widths ranging from about 0.001 inch (0.003 cm) to about 0.035 inch (0.089 cm), and thicknesses ranging from about 0.00025 inch (0.0006 cm) to about 0.002 inch (0.005 cm).

In accordance with the present invention, apertured films of the type disclosed in the above mentioned Turi et al. applications are modified so as to provide the film with improved fluid distribution properties in the region of the film which have been subjected to stretching, by downward deflection of the film into the recessed region of the support member, during formation of the film.

The method for forming an apertured film from a stretchable thermoplastic polymeric material in accordance with the invention comprises the steps of providing a starting film comprising said stretchable thermoplastic polymeric material and having an upper surface and a lower surface. A backing member comprising localized support regions for supporting the starting film is provided. The backing member has recessed zones into which the film may be deformed by the application thereto of fluid forces. Means for allowing said applied fluid to be transported away from the backing member are provided.

The starting film on the backing member has portions of the lower surface of the film being in contact with the support regions of the backing member. The upper surface of the film faces away from the backing member.

A fluid in the form of columnar streams from at least two sets of orifices is directed against the upper surface of the starting film in a zone of contact, i.e., a zone in which the film is subjected to the forces from the fluid streams. The orifices of the first set each have a diameter greater than ten mils and the fluid supplied thereto has a pressure less than 500 psig. to cause the formation of large sized holes in said starting film. The orifices of the second set each have a diameter less than or equal to ten mils and the fluid supplied thereto has a pressure of at least 500 psig. to cause the formation of micro-holes in the starting film.

The film is removed from the contact zone, and the now-apertured film is removed from the backing member.

Other features and advantages of the present invention will become readily apparent from the following detailed description, the accompanying drawings, and the appended claims.

BRIEF DESCRIPTION OF THE DRAWINGS

FIG. 16 is an end elevational view of the apertured film of FIG. 15;

FIG. 17 is an end elevational view of the apertured film of FIG. 15 at a magnification of 15 times;

DESCRIPTION OF THE PREFERRED EMBODIMENTS

Figure 1:
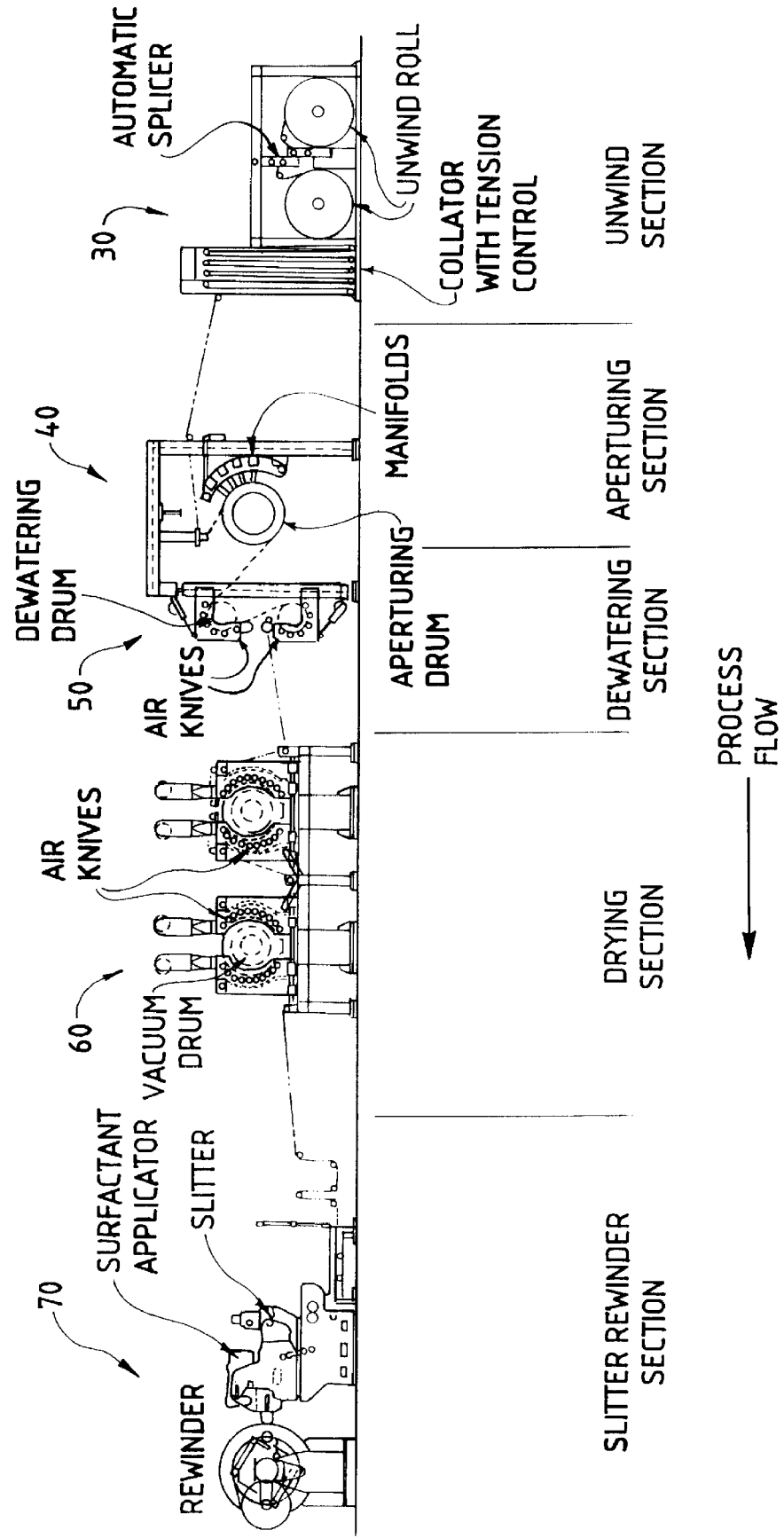
FIG. 1 is a schematic side elevational view of a production line for forming apertured film in accordance with the present invention.

While the present invention is susceptible of embodiment in various forms, there is shown in the drawings and will hereinafter be described presently preferred embodiments, with the understanding that the present disclosure is to be considered as an exemplification of the invention, and is not intended to limit the invention to the specific embodiments illustrated.

Referring now to the drawings, FIG. 1 is a schematic, side elevational view of one embodiment of a production line that may be utilized to produce apertured films in accordance with the teachings of the present invention. As is indicated by the direction arrow, the process flow proceeds from right to left in FIG. 1. As is shown in FIG. 1, the production line has five major stations; a film unwinding station 30, an aperturing station 40, a dewatering station 50, a drying station 60, and a slitting, rewinding, and surfactant application station 70.

Figure 2:
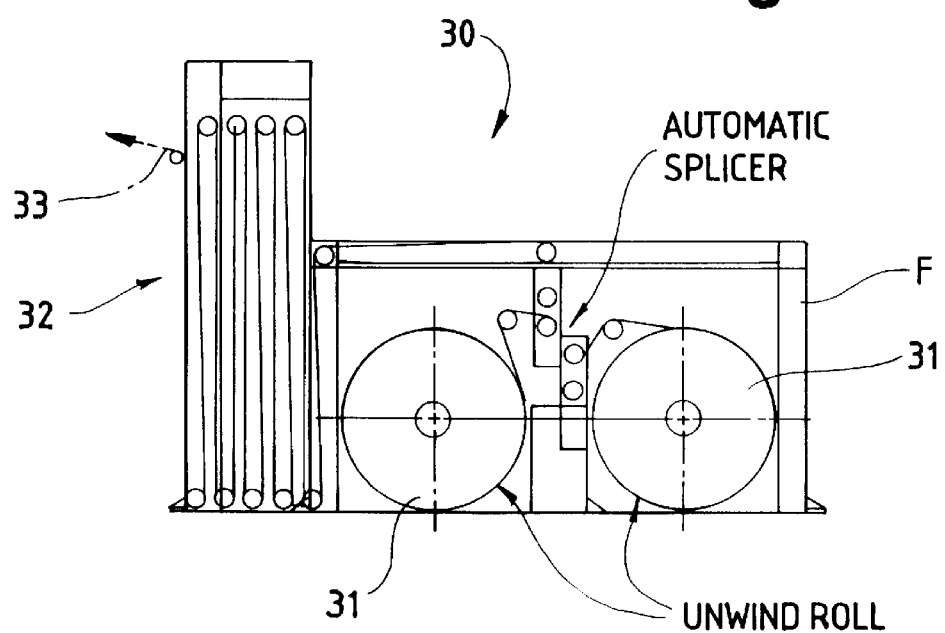
FIG. 2 is a schematic side elevational view, on an enlarged scale, of the unwind section of the apparatus for producing the apertured film of the present invention.

As shown in FIG. 2 in the film unwinding station, two rolls 31 of starting film material 33 are mounted for rotation on frame F. The film from rolls 31 is fed over guide rollers and into festoon 32 which has an automatic (closed loop) tension control system. Film 33, under suitable tension, e.g., between 0.1 to 1 pound per linear inch, emerges from festoon 32, and proceeds to the aperturing station 40.

While many different starting film materials are suitable for use in the present invention, one of the preferred materials is a polyethylene film commercially available from Exxon Chemical under product designation EMB-631. This film is an embossed, white pigmented polyethylene film. The polyethylene component consists of a blend of 40% by weight low density polyethylene and 60% by weight linear low density polyethylene. The film has 6.5% by weight titanium dioxide.

The starting film is embossed with a diamond pattern at 165 lines per inch to provide on one side of the film, referred to as the male side, a plurality of discontinuous observable protrusions separated by a continuous, interconnected grooved pattern. The other side of the embossed starting film, referred to as the female side, has a plurality of observable, cupped recesses separated by a continuous, interconnected rib pattern. The cupped recesses in the female side of the film are in respective registration with the protrusions on the male side of the film. The starting film is electrostatically treated with a corona discharge treatment on one side, preferably the male side. The film has an ultimate tensile strength of 1750 grams in the machine direction (with 500% elongation at break), and 1300 grams in the cross direction (with 650% elongation at break), as determined using ASTM test D-882.

The process for making the film of the invention may be either batch or continuous, generally similar to the batch and continuous processes disclosed in co-pending Ser. No. 08/417,404 U.S. Pat. No. 5,567,376. The preferred embodiment is a continuous apparatus, as further disclosed herein.

Figure 3:
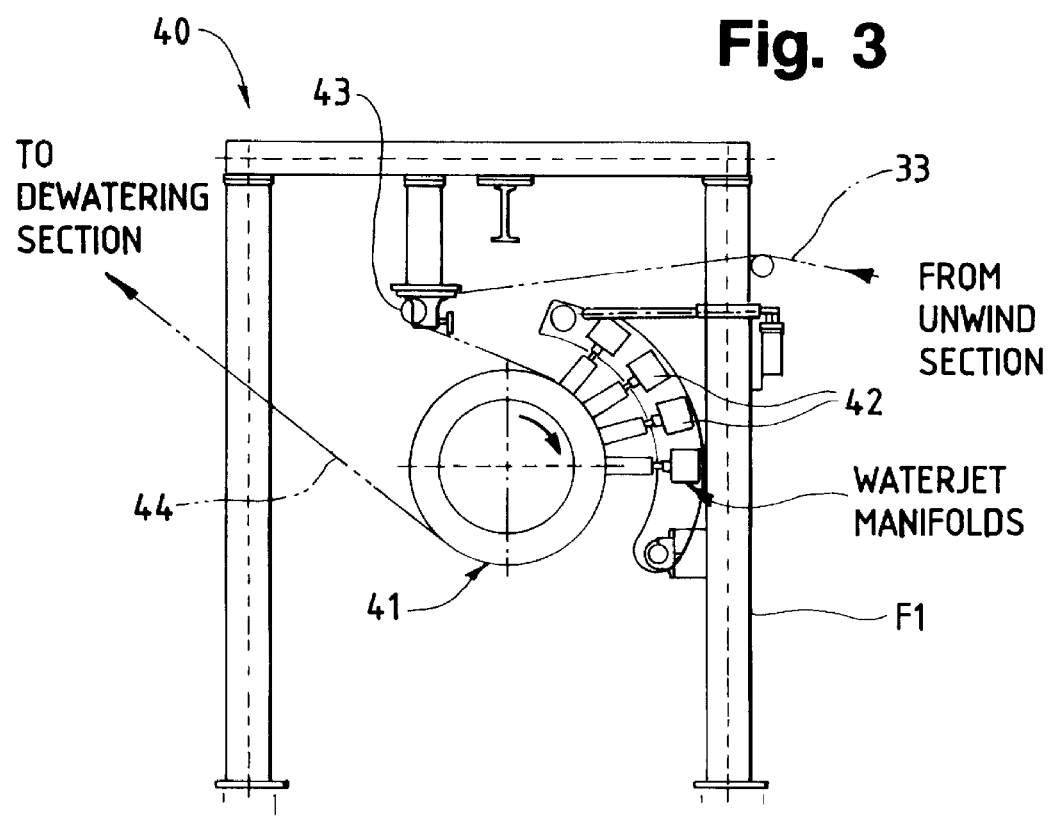
FIG. 3 is an enlarged side elevational view of the aperturing section of the apparatus used to form the apertured film of the present invention.

With reference to FIG. 3, the film 33 from the unwind station is shown entering aperturing station 40 at the right hand side thereof. Aperturing station 40 includes a honeycomb-type support drum 41 rotatably mounted on a frame F1. The drum 41 has a three-dimensional backing or forming member, described in detail hereinafter, mounted on its outer peripheral surface. Four water jet manifolds 42 are also supported on frame F1 and four suction slots, one for each manifold 42, are provided interiorly of the support drum, as is also hereinafter described in detail. The suction slots are mounted within the drum and are aligned with the water jet manifolds located outside of the drum. Each water jet manifold comprises a metallic strip, hereinafter sometimes referred to as an orifice strip, having a plurality of orifices having predetermined size and spacing. Specific examples of such orifice strips are described in more detail hereinafter. A given manifold 42 may comprise one or more orifice strips. The orifice size preferably remains constant for each strip. However, the orifice size may vary on a given strip. The distance between the lower surface of the orifice strip and the outer surface of the backing member of the aperturing drum is preferably in the range of between 0.50 to 1.0 inches.

Hot water under pressure is pumped to the manifolds 42, and the pressurized water exits through the plurality of orifices in the orifice strip in the form of columnar water jets. The water pressure in each manifold 42 may be separately regulated. The entering film 33 is trained over a guide roller 43, and then over the outer periphery of the three dimensional forming member mounted over the support drum 41. The columnar streams of water exiting the orifice strips impinge on the film and cause the film to deflect downwardly into the recessed regions of the backing member mounted on the support drum, thereby causing the film to stretch and rupture into a multiplicity of irregular size holes. The now-apertured film 44 emerges from aperturing station 40 at the left-hand side thereof and passes to dewatering section 50.

Figure 4:
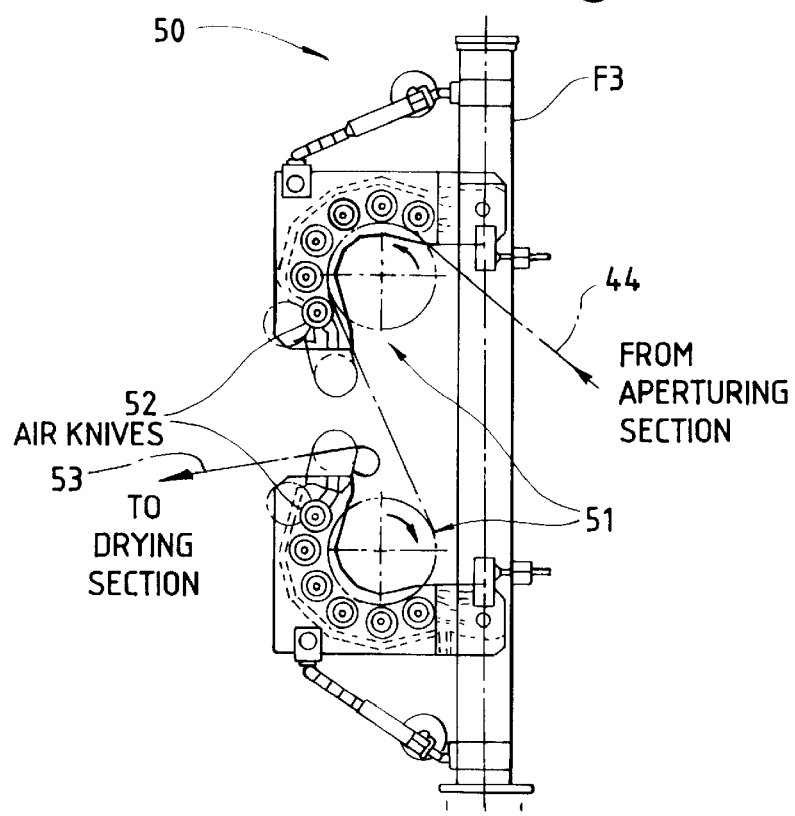
FIG. 4 is an enlarged side elevational view of the dewatering section of the apparatus used to form the apertured film of the present invention.

As is shown in FIG. 4, in the dewatering section 50, two dewatering drums 51 are mounted for rotation on frame F3. Drums 51 have a honeycomb configuration, and each drum has two vacuum slots associated therewith, capable of drawing vacuum up to 7 inches Hg. Twelve air knives 52 are provided, six air knives being provided for each drum 51. The suction slots associated with the dewatering drums 51 are located internally of the drums, whereas air knives 52 are located outside of the drums 51. Excess water is removed from the apertured film by the impingement of high velocity air from knives 52 and by suction through the suction slots in drums 51. Air knives 52 operate at an air temperature range between about 150°–180° F. Total air flow through the twelve air knives 52 is between about 1,000 to about 2,000 cubic feet per minute per linear foot of apertured film width. The dewatered film 53 emerges from the dewatering station 50, at the left-hand side thereof, and passes to the drying section.

Figure 5:
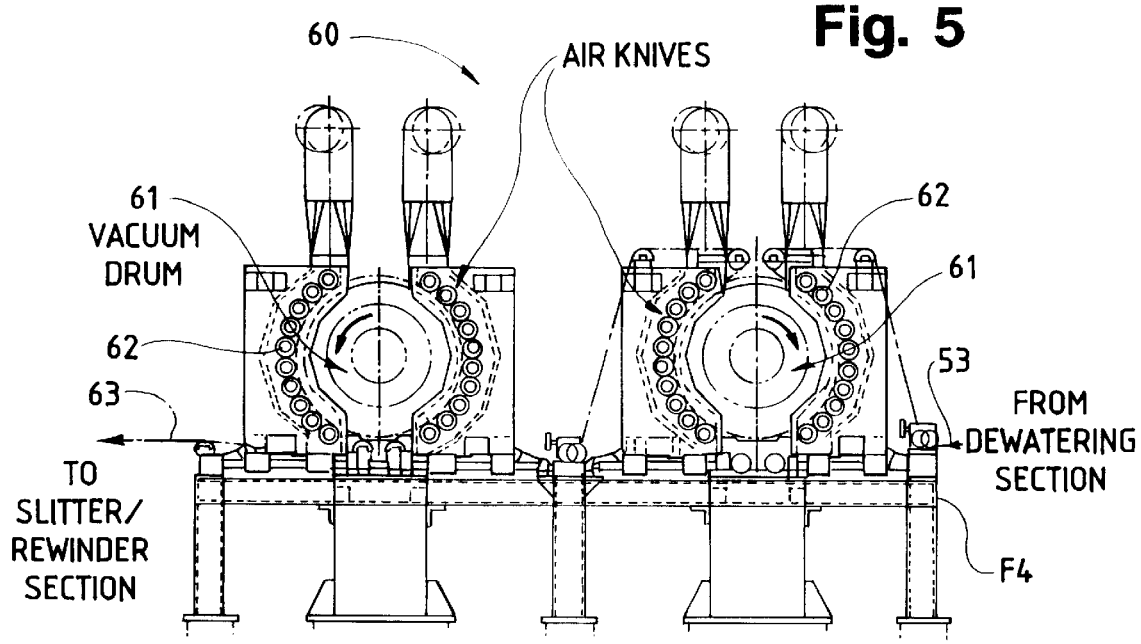
FIG. 5 is an enlarged side elevational view of the drying section of the apparatus used to form the apertured film of the present invention.

With reference to FIG. 5, the air drying station 60 is illustrated as including two vacuum drums 61 mounted on frame F4. Each drum 61 has a suction slot, which has an arc of 300° around the drum. Twenty air knives 62 are positioned outwardly of each vacuum drum 61 and the air knives 62 operate at a temperature between 150°–180° F. The combined air flow for all forty air knives 62 is between about 5,000 to about 7,000 cfm per linear foot of apertured film width. The pressure drop caused by the vacuum in drums 61 is about 2 inches of water measured across the film. The dried film 63 emerges from drying section 60 at the left-hand side thereof and passes to slitter/rewinder section 70.

Figure 6:
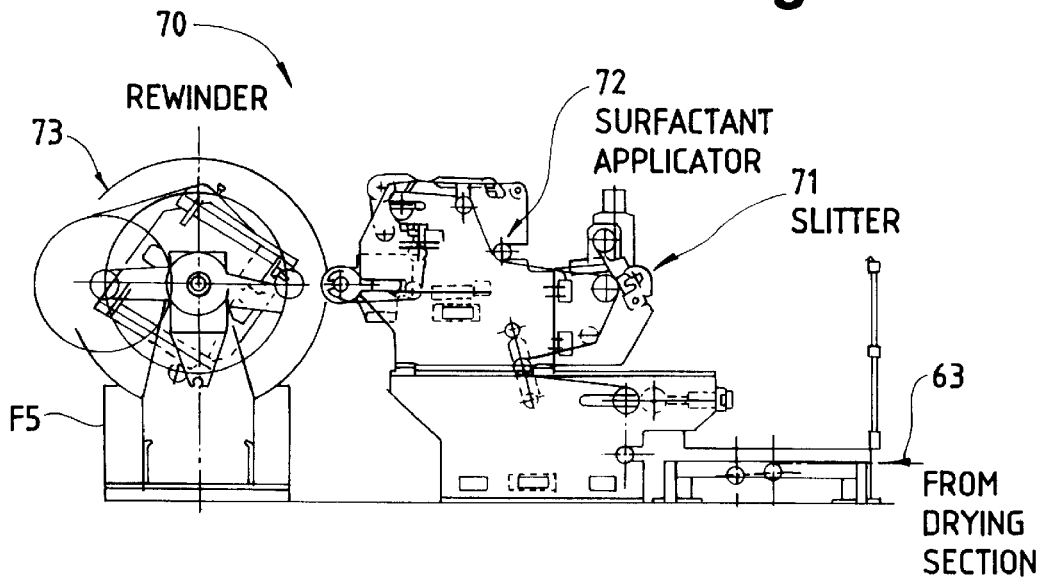
FIG. 6 is an enlarged side elevational view of the slitter/rewinder section of the apparatus used to form the apertured film of the present invention.

Referring now to FIG. 6, the film 63 from the drying section enters the slitter/rewinder station 70 at the right hand side thereof. A slitter 71, consisting of spaced score cut type slitting knives, cuts the dried apertured film to the desired width. The dried and slit apertured film then passes to a surfactant applicator 72, where a suitable surfactant, e.g., Tween 20, is applied to the film by kiss-coating. The surfactant is preferably provided in an aqueous solution consisting of about 48.8±1.5 percent surfactant. In an exemplary embodiment of the invention, the surfactant roller coating speed is 15±3 inches per minute. Preferably, the surfactant is applied to the male side of the film. The above-mentioned parameters result in a surfactant solution add-on of 0.25 mg/in$^2$±0.07.

Referring to FIGS. 7A–7E, the columnar jets of water are discharged from one or more orifice strips having a plurality of orifices. Preferably, the orifices are formed by drilling a precursor metallic strip to form cylindrical holes. However, it is anticipated that holes of various shapes may be used.

Figure 7A:
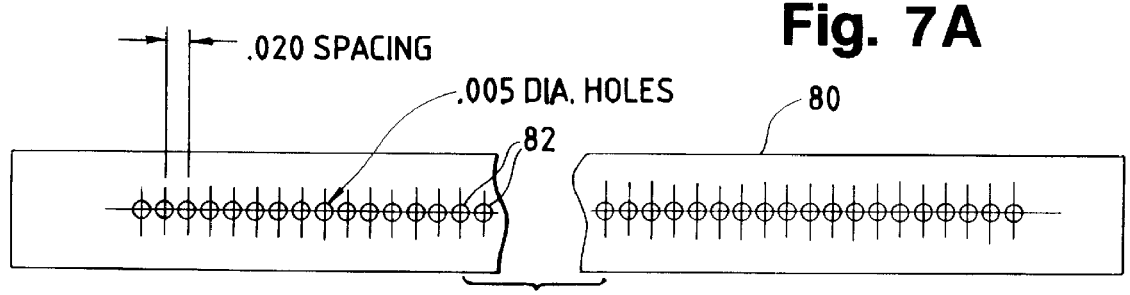
FIG. 7A is a schematic view of an orifice strip used in the apparatus to form one of the apertured films of the present invention.

FIG. 7A shows an orifice strip 80 for delivering columnar jets of water each having a relatively small cross-section to form micro-holes in the film. The orifices 82 in the manifold have a diameter of 5 mils (0.005 inch), and are spaced 0.020 inch apart. This manifold strip is available from the Nippon Nozzle Co., of Kobe, Japan.

Figure 7B:
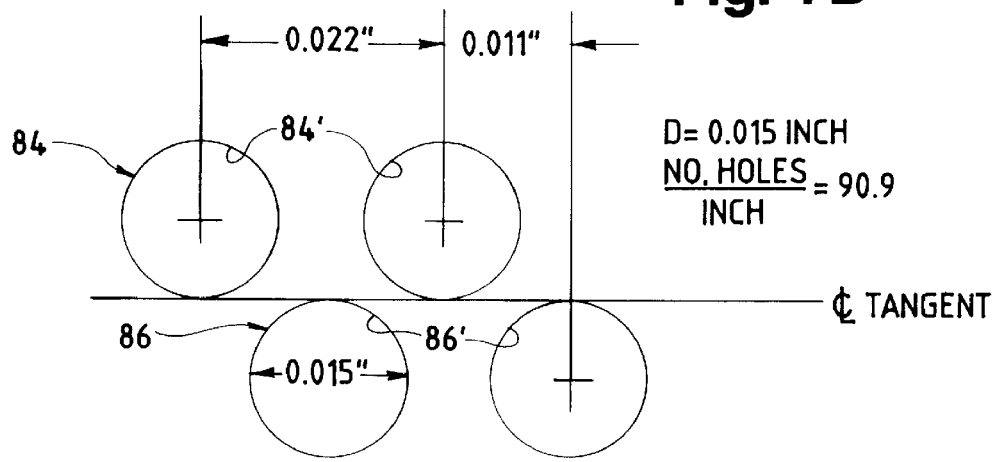
FIGS. 7B, C, D and E are enlarged views of orifice patterns which can be used in the apparatus to form the apertured films of the present invention.

FIGS. 7B–7E show orifice strips for producing columnar jets of water, each having a relatively large cross section, to form large sized holes in the film. FIG. 7B shows an orifice strip having two rows 84, 86 of orifices 84', 86' that are spaced apart on opposite sides of a center tangent line. The orifices in each row have a diameter of 15 mils (0.015 inch), and are spaced 0.022 inch apart, center-to-center. The spacing of the orifices in the top row is offset from the spacing of the orifices in the bottom row by 0.011 inch. The strip contains 90.9 orifices per inch.

Figure 7C:
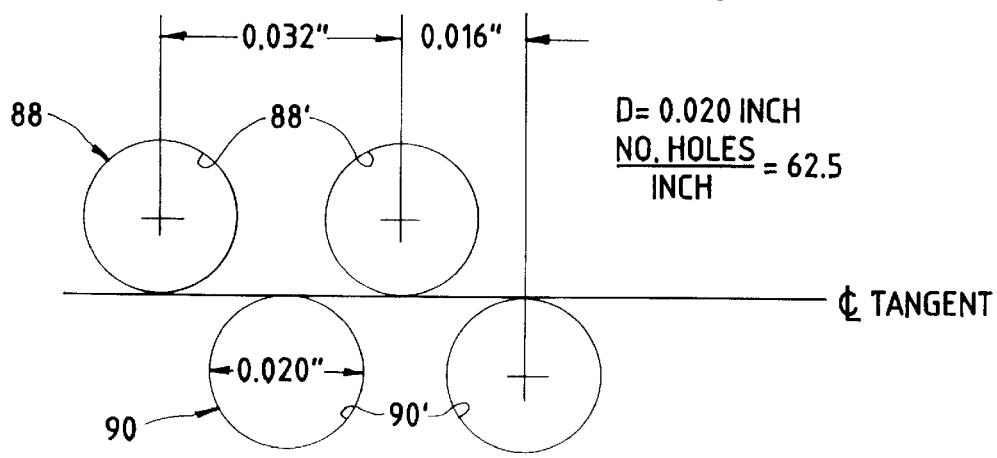

FIG. 7C shows an orifice strip having two rows 88, 90 of orifices 88', 90' that are spaced apart on opposite sides of a center tangent line. The orifices in each row have a diameter of 20 mils (0.020 inch), and are spaced 0.032 inch apart. The spacing of the orifices in the top row is offset from the spacing of the orifices in the bottom row by 0.016 inch. The strip contains 62.5 orifices per inch.

Figure 7D:
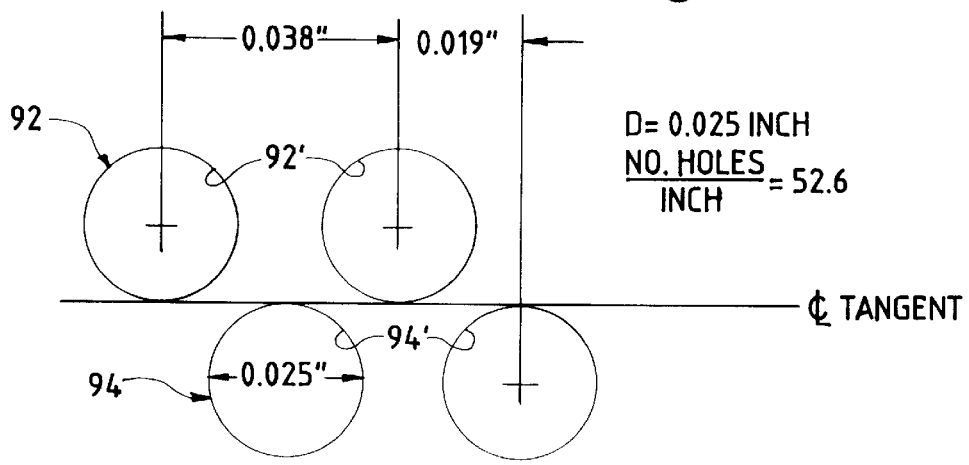

FIG. 7D shows an orifice strip having two rows 92, 94 of orifices 92', 94' that are spaced apart on opposite sides of a center tangent line. The orifices in each row have a diameter of 25 mils (0.025 inch), and are spaced 0.038 inch apart. The spacing of the orifices in the top row is offset from the spacing of the orifices in the bottom row by 0.019 inch. The strip contains 52.6 orifices per inch.

Figure 7E:
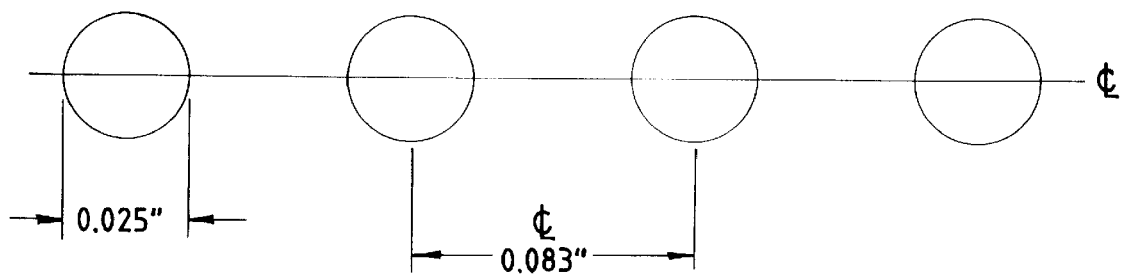

FIG. 7E shows an orifice strip for delivering columnar jets of water each having a relatively large cross-section for forming large sized holes in film. The orifices each have a diameter of 0.025 inches, and are spaced 0.083 inches, center-to-center. While the orifice strip shown in FIG. 7E is suitable for forming film in accordance with the present invention, use of orifice strips such as shown in FIG. 7B–7D is presently preferred for use in combination with one or more orifice strips having relatively small orifices for formation of micro-sized holes.

The small orifices (see FIG. 7A) preferably have a diameter under 10 mils. The larger orifices (see FIGS. 7B–7E) preferably have a diameter greater than 10 mils.

An apparatus for making apertured films of the present invention is described in detail in co-pending patent application Ser. No. 08/417,404. The apparatus for making the film of the present invention contains certain additional features, including a second set of orifice strips as discussed above with reference to FIGS. 7B–7E. The pressure of the water delivered to the small orifices is generally greater than 500 psig, preferably on the order of 500–1600 psig or higher. The pressure of water delivered to the large orifices is generally less than 500 psig, preferably on the order of 125–200 psig.

Figure 8:
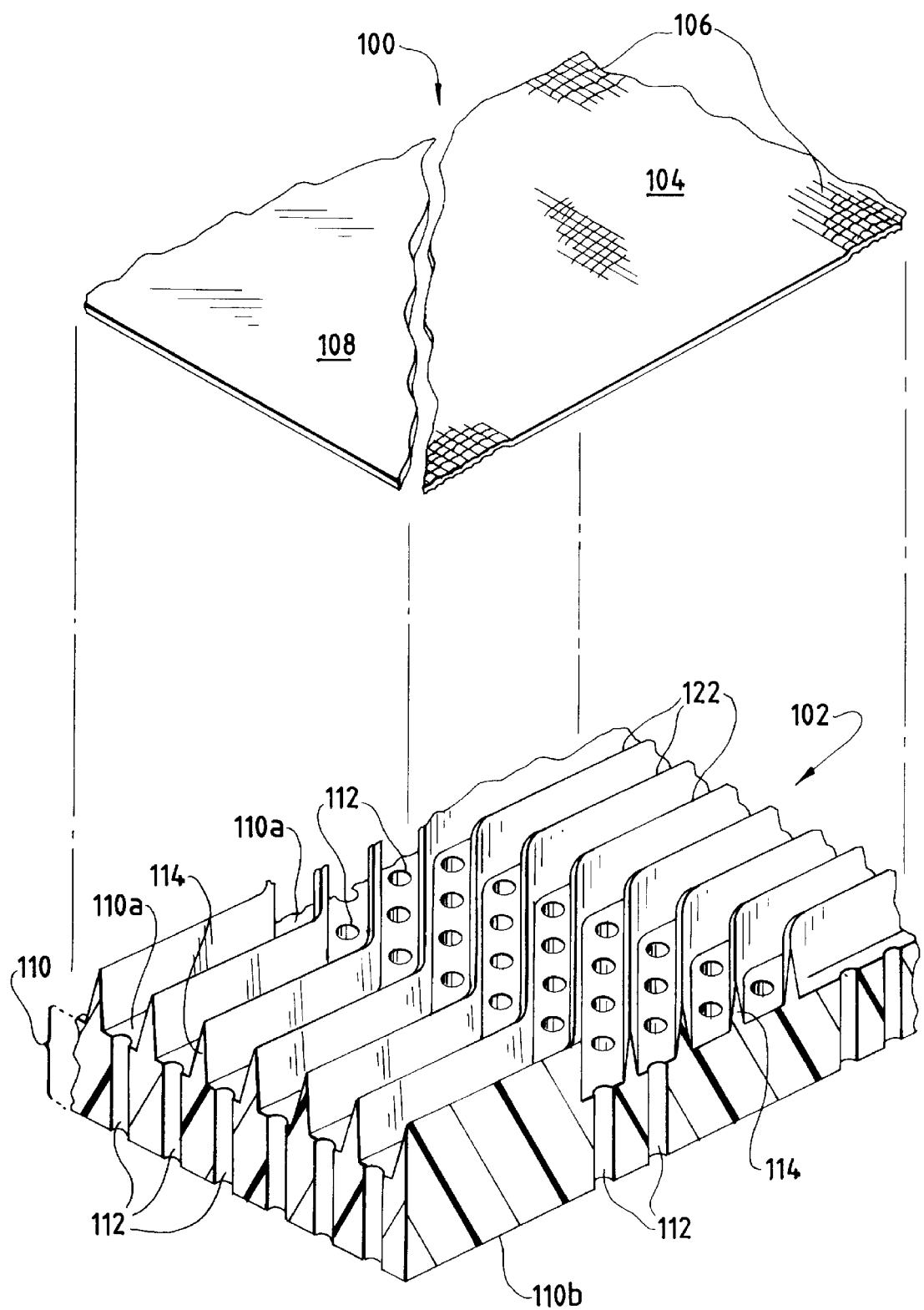
FIG. 8 is an exploded perspective view of a starting film positioned on a backing member for processing in accordance with the present invention.
Figure 9:
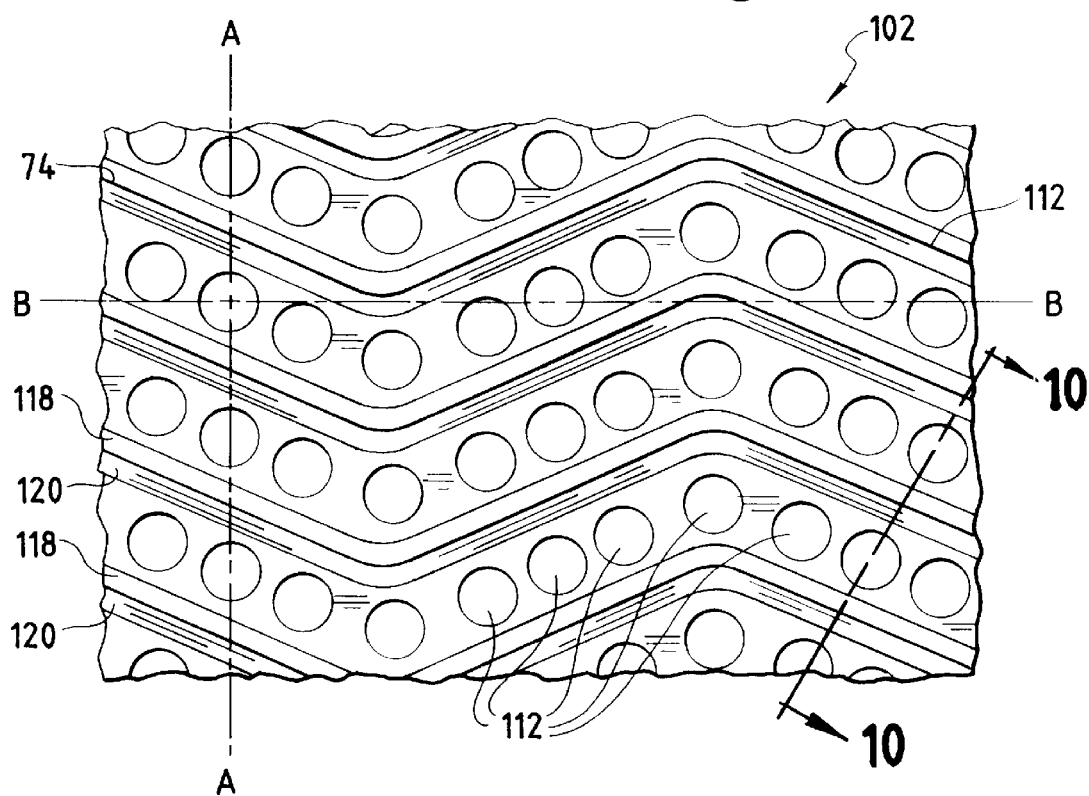
FIG. 9 is a top plan view of the backing member shown in the lower portion of FIG. 8.
Figure 10:
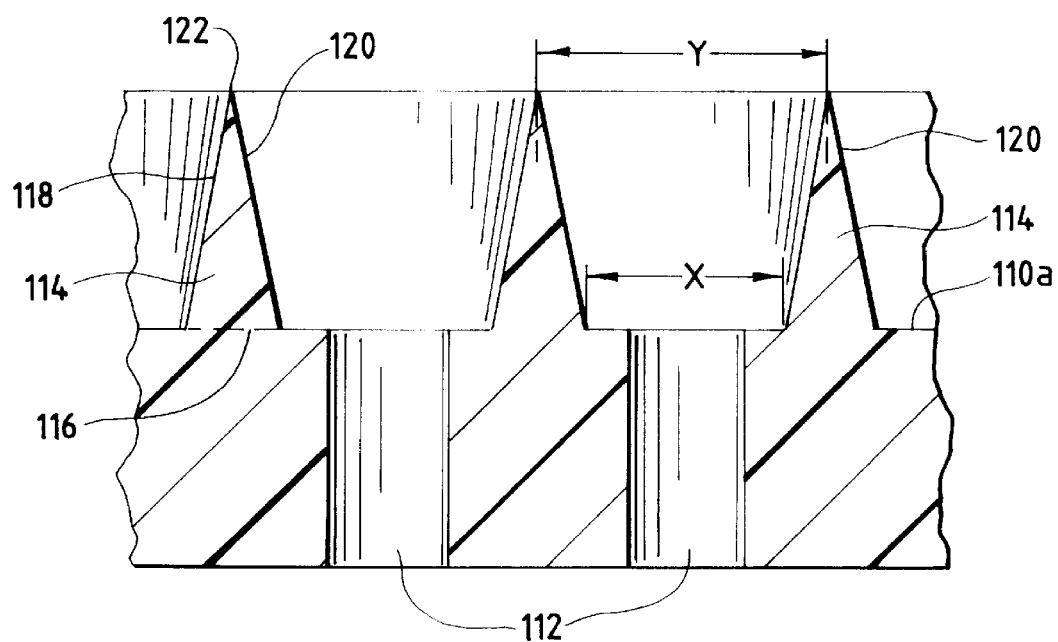
FIG. 10 is an enlarged cross-sectional view taken along line 10—10 of FIG. 9.

In a preferred embodiment, the aperturing equipment consists of a honeycomb type support drum, a three dimensional forming member, several water jet manifolds, and corresponding suction slots arranged interiorly of and sequentially along a section of the circumference of the drum. The forming member is an engraved sleeve, as shown in FIGS. 8–10, which is mounted onto the honeycomb support drum. The suction slots are mounted within the drum and they are lined up with the water jet manifolds located outside the drum. Each water jet manifold contains a metallic strip having a plurality of orifices. For a given manifold, the orifice size remains constant throughout the strip. The distance between the orifice strip and the surface of the engraved sleeve is preferably between 0.50 to 1 inch. The manifolds are pressurized by pumping in heated water. The pressurized water exits through the series of orifices in the orifice strip, thus creating substantially columnar water jets. The energy of the columnar hot water jets impinging on the film causes the film to contour toward the surface of the engraved sleeve thereby causing the film to stretch and rupture into a multiplicity of irregular size holes. The pressure and temperature of the water supplied to each manifold may be separately regulated. The process parameters are as follows:

Line Speed (yards/min): 50–200

Water Temperature: 155°–165° F.

Maximum Number of Manifolds Used: 3

Distance between Manifold Strip and Surface of Sleeve: 0.50"–1"

Low Pressure Manifold:

Number of Manifolds: 1

Orifice Size Range (inch): 0.0145 to 0.030

Pressure (psig): 150±25

Water Flow: 8.0±2.0 gallons per minute per inch of orifice strip (gpm/in)

Suction Slot Vacuum (inch of Hg): 5.0±2.0 (−17±10.2 kPa)

High Pressure Manifold:

Number of Manifolds: Maximum of 2

Orifice Size Range (inch): 0.005 to 0.007

Pressure (psig): 1,150±350

Water Flow: 0.9±0.22 gallons per minute per inch of orifice strip

Suction Slot Vacuum (inch of Hg): 5±3 (−17±10.2 kPa)

Manifold Usage Sequence:

The pressurized water jet manifolds and their associated orifice strips can be arranged in a variety of sequences relative to the direction of continuous travel of the film on the drum. Any of the following five sequences may be used to aperture the film:

1. Low Pressure, High Pressure
2. Low Pressure, High Pressure, High Pressure
3. High Pressure, Low Pressure
4. High Pressure, Low Pressure, High Pressure
5. High Pressure, High Pressure, Low Pressure Referring to FIGS. 8–10, the forming member is a three dimensional surface having a plurality of radially extending support elements that rise from the base of the forming or backing member. These elements are substantially similar to the corresponding elements disclosed in co-pending patent application Ser. No. 08/417,404 U.S. Pat. No. 5,567,376.

FIG. 8 is an exploded perspective view of starting film 100 supported on backing member 102. The starting film may be either embossed or unembossed. Alternatively, a portion 104 of starting film 100 comprises embossments 106, and unembossed regions 108 as shown in the upper portion of FIG. 8.

Backing member 102 comprises a base portion 110 having an upper surface 110a and a lower surface 110b. Backing member 102 further comprises a plurality of apertures 112 running through the thickness of base 110 from upper surface 110a to lower surface 110b. As will be seen hereinafter, apertures 112 are provided to allow for removal of water during the manufacture of apertured film according to the invention. Backing member 102 also includes a plurality of radially-extending support elements 114. These support elements comprise a base 116 coinciding with the plane of upper surface 110a of portion 110 and a pair of angled side walls 118, 120 (best seen in FIGS. 9 and 10). Side walls 118, 120 extend outwardly from base 116 to meet at a land portion or ridge 122. Support elements 114 are aligned in parallel and spaced equidistantly from one another. They may run either parallel to, perpendicular to, or at any angle to the sides of the backing member. As shown in FIGS. 8 and 9, these support elements 114, when viewed in plan, are generally sinusoidal-like or wavy in configuration. It will be understood that the support elements may be provided in other configurations, e.g., straight-line, zig-zag and the like. A detailed description of the forming member is disclosed in co-pending patent application Ser. No. 08/417,404 U.S. Pat. No. 5,567,376.

Figure 11A:
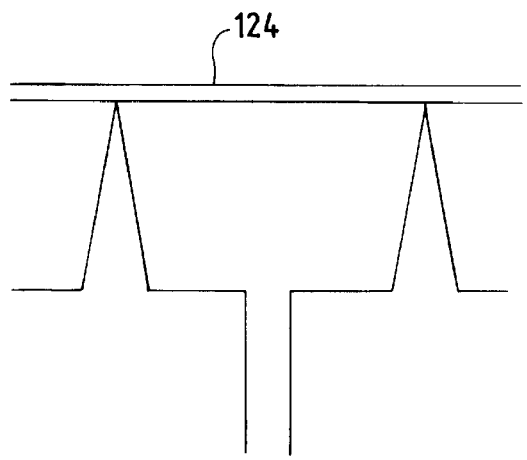
FIGS. 11A, B, C, D are views similar to FIG. 10 showing sequential stages in the drawing of the starting film to form apertures in accordance with the teachings of the present invention.
Figure 11B:
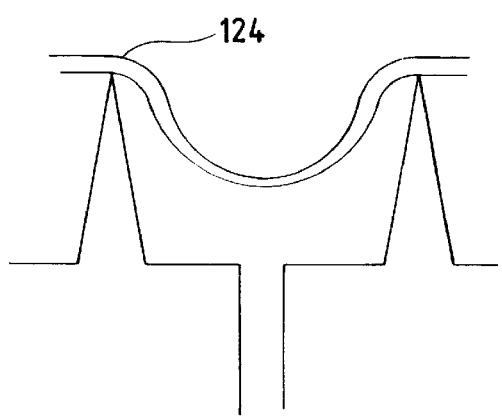
Figure 11C:
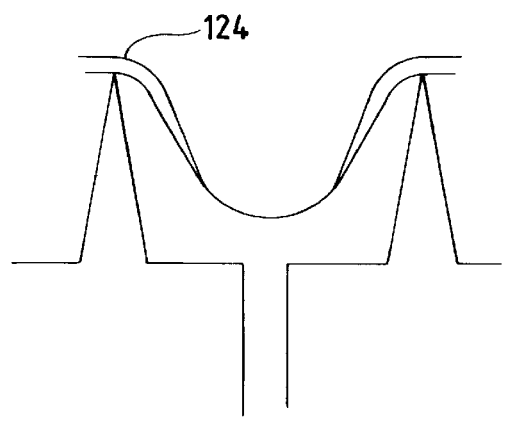
Figure 11D:
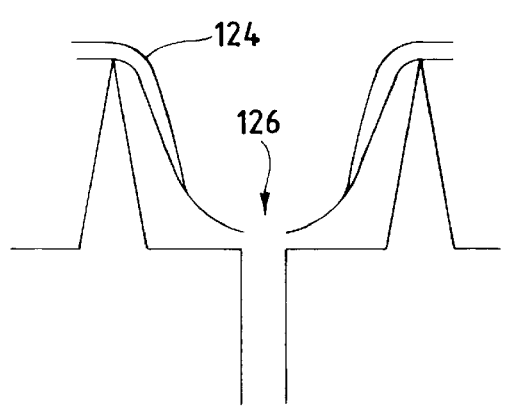
Figure 12:
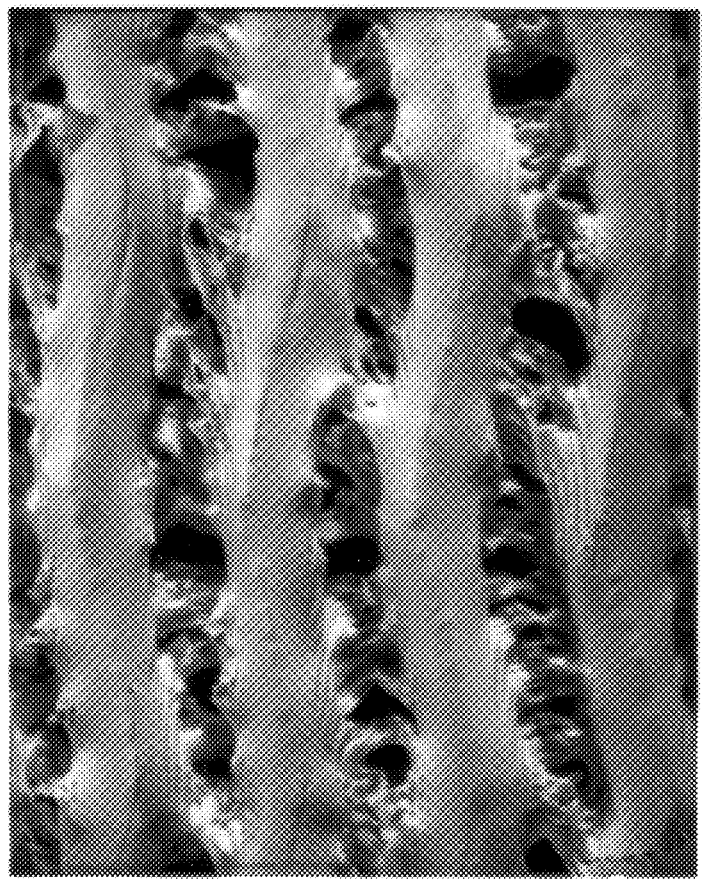
FIG. 12 is a photograph in top plan of an apertured film formed in accordance with the present invention at a magnification of 7.5 times.
Figure 13:
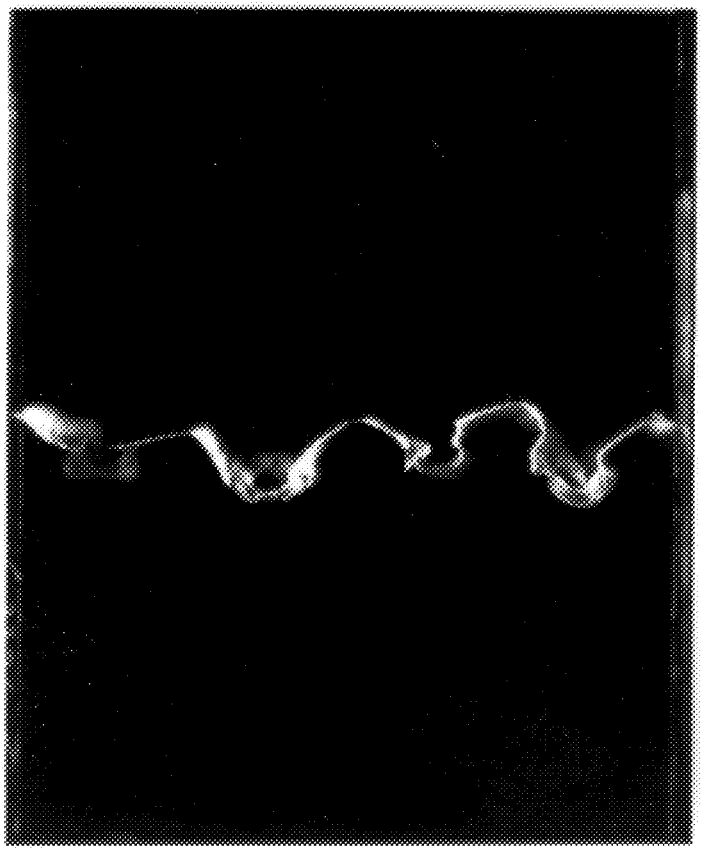
FIG. 13 is an end elevational view of the apertured film of FIG. 12.
Figure 14:
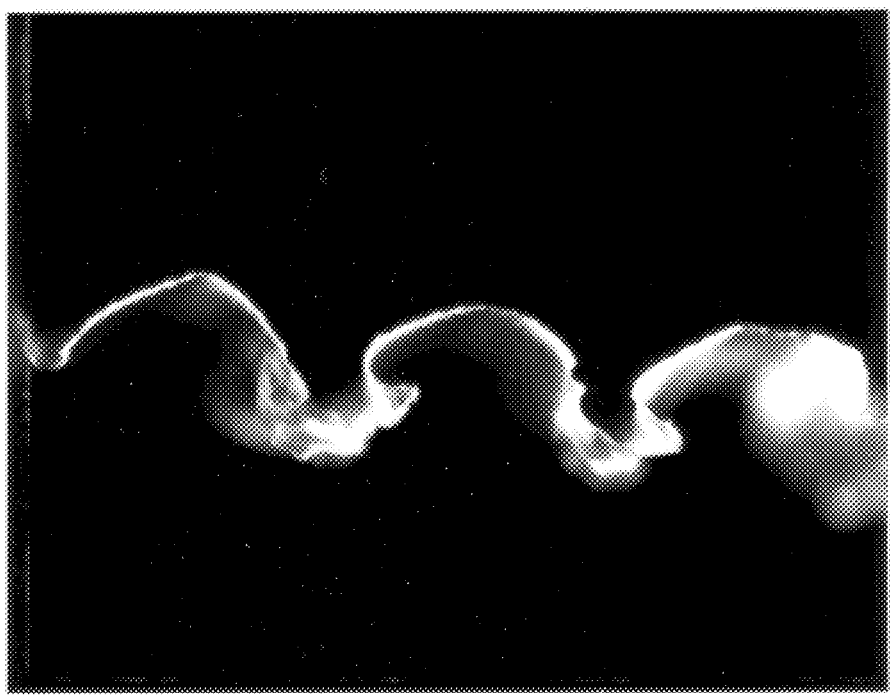
FIG. 14 is an end elevational view of the apertured film of FIG. 12 at a magnification of 15 times.
Figure 15:
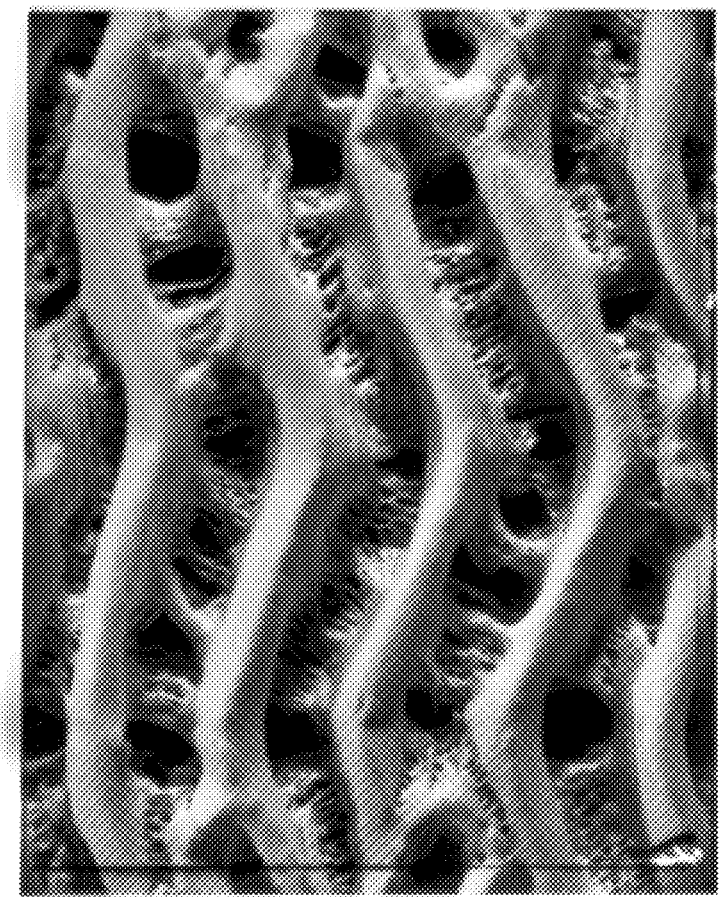
FIG. 15 is a top plan view of another apertured film formed in accordance with the teachings of the present invention at a magnification of 7.5 times.

Referring to FIGS. 11A–D, the progression of the drawing of the starting film 124 to form apertures in accordance with the teachings of the present invention are shown. Referring to FIG. 11A, the starting film 124 is initially laid on the backing member. Referring to FIG. 11B, the film 124 deforms in response to the application of columnar jets of water and is drawn (i.e., stretched) downwardly and partially into the space between support elements. Referring to FIG. 11C, as the film 124 is drawn, it becomes thinner. Referring to FIG. 11D, as the film is further drawn and becomes thinner, it begins to break apart and form holes 126. This process is further described in co-pending patent application Ser No. 08/417,404 U.S. Pat. No. 5,567,376, wherein the formation of micro-holes surrounded by micro-strips of film material, or fibrils, is described.

Due to the vertical elements on the forming member, the film of the present invention is expanded (i.e., is given significant dimensionality in the z-direction relative to the original thickness of the precursor unapertured film) immediately as it comes off the process. In some prior art processes, expansion in the z-direction must be accomplished in a separate embossing step (see for example, U.S. Pat. No. 4,609,518). An expanded topsheet limits the contact between the wearer and the absorbent layer and thus enhances the feeling of dryness in products that incorporate it.

In the films, absorbent products and methods disclosed herein, the holes in the film include both micro-holes and large sized holes, or may include large sized holes only. It is believed that the micro-holes are formed primarily from the drawing of film material in response to application of columnar jets of water coming from the smaller orifices of the orifice strip discussed above. It is believed that the large sized holes, also formed from the drawing of film material, are formed primarily in response to application of the columnar jets of water coming from the larger orifices, rather than the smaller orifices, of the orifice strip discussed above.

Figure 18A:
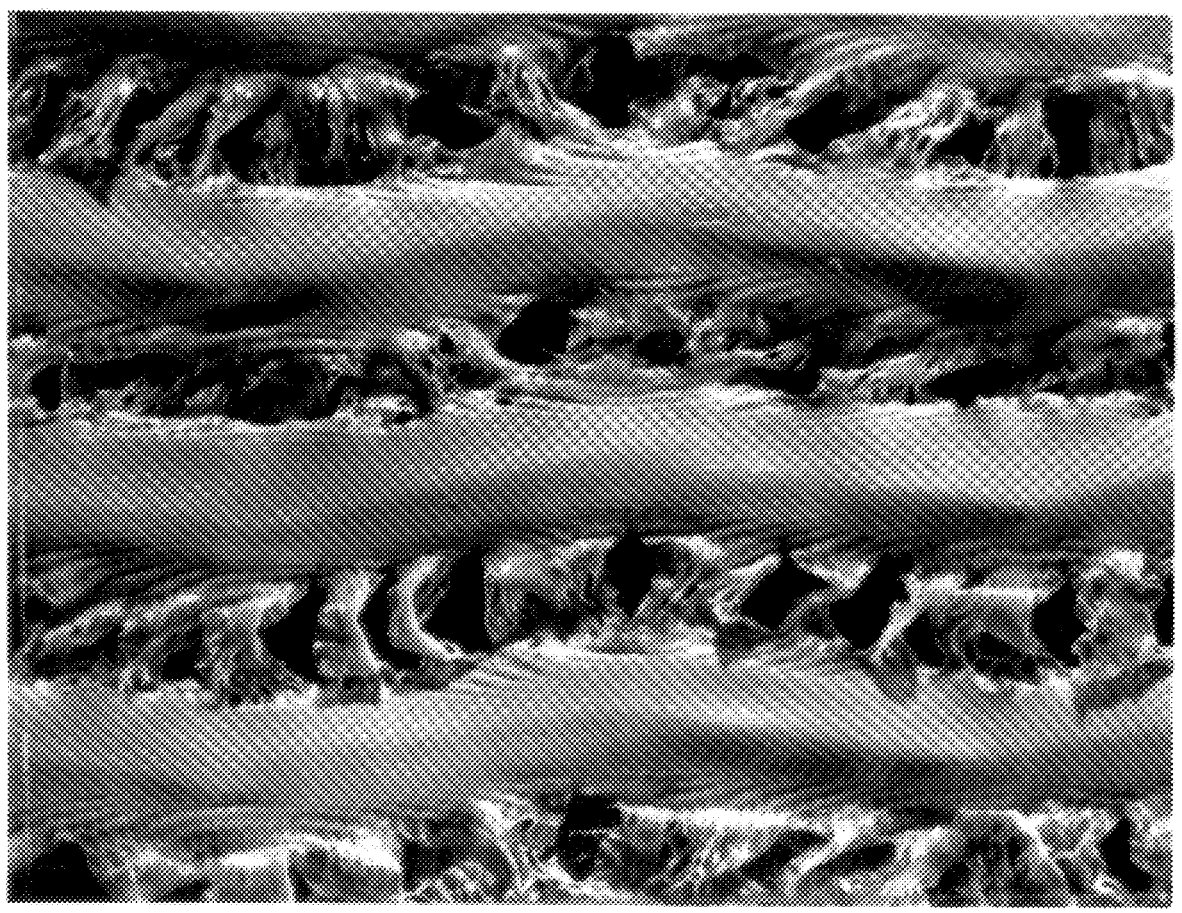
FIGS. 18A and B are photographs taken at a magnification of 10× of apertured film formed in accordance with the invention, formed from an embossed starting film having the female side thereof against the associated forming member, wherein the film was subjected to aperturing by a sequence of three orifice strips, the first having relatively large orifices in accordance with FIG. 7D, and the second and third having relatively small orifices in accordance with FIG. 7A (FIG. 18A being the side thereof against which the water jets were directed, FIG. 18B being the side thereof positioned against the associated forming member)
Figure 18B:
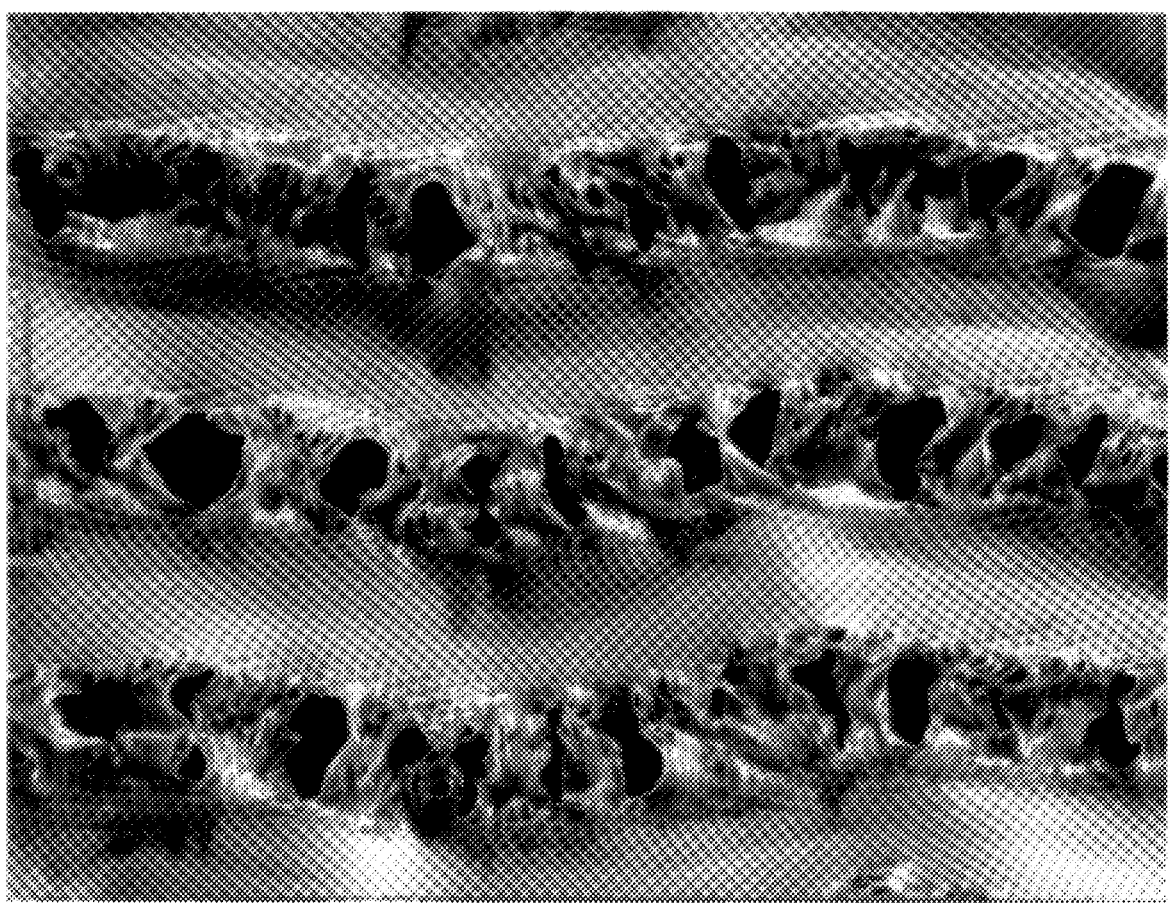
FIGS. 18C and D are photographs taken at a magnification of 10× of apertured film formed in accordance with the invention, formed from an embossed starting film having the female side thereof against the associated forming member, wherein the film was subjected to aperturing by a single orifice strip having relatively large orifices in accordance with FIG. 7D (FIG. 18C showing the side thereof against which the water jets were FIG. 18D showing the side thereof positioned against the associated forming member)
Figure 18C:
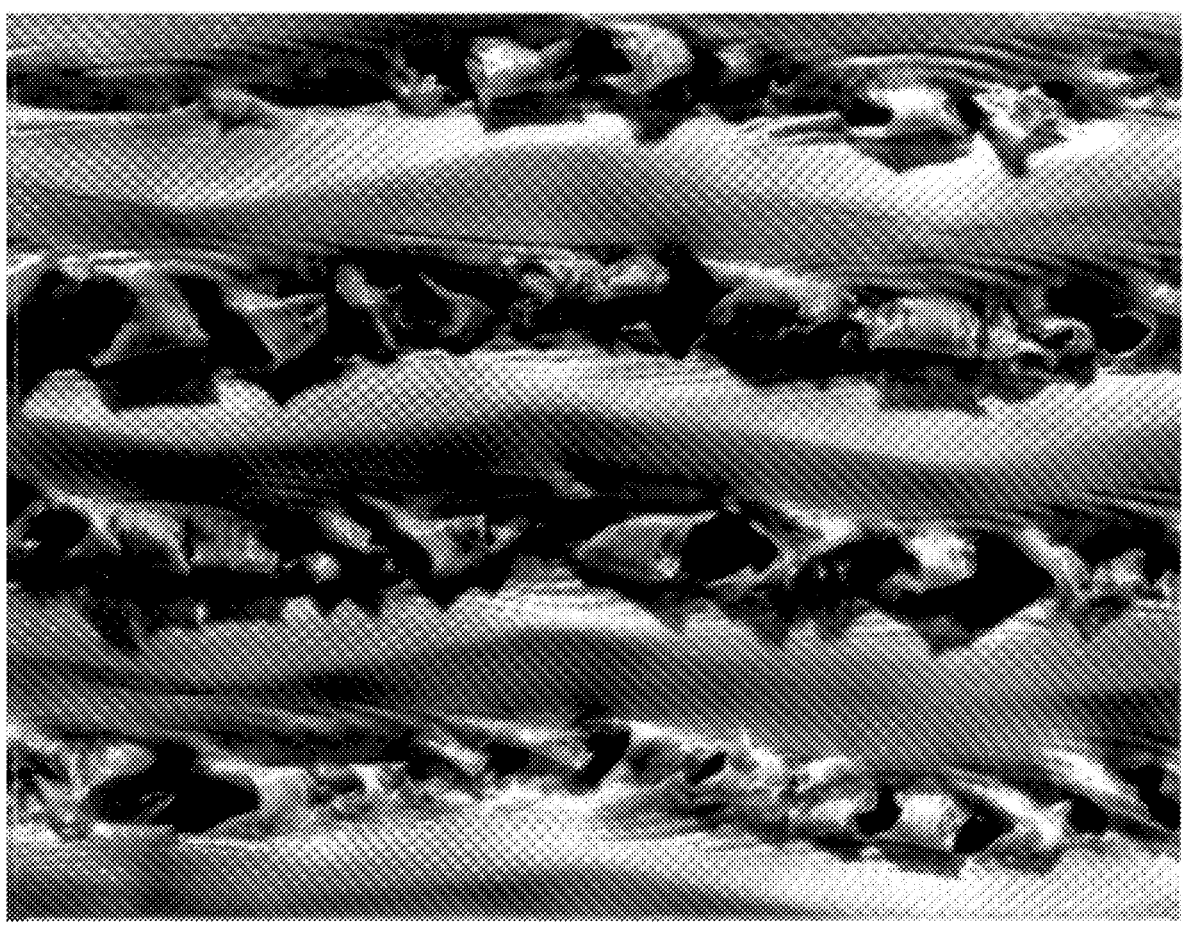
Figure 18D:
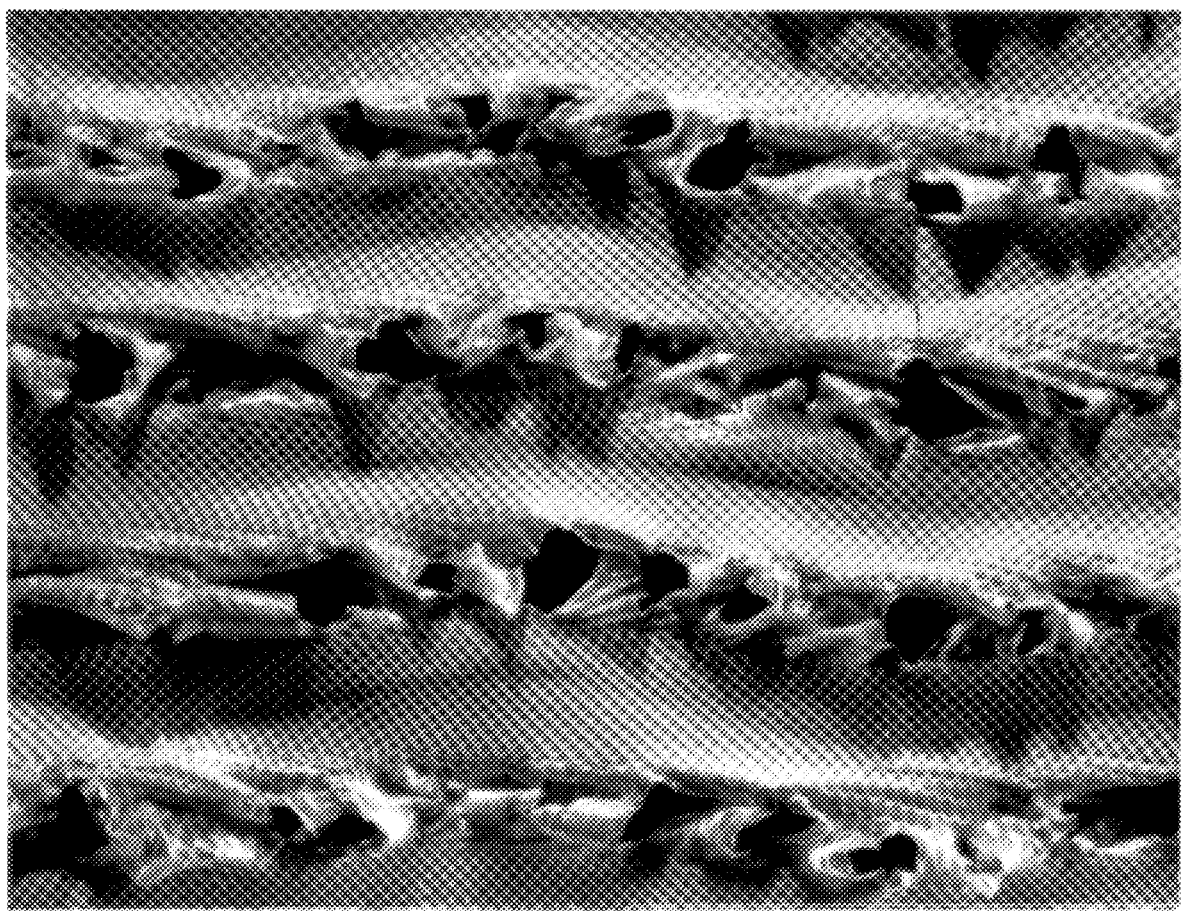

The resulting apertured film has a combination of large sized holes or apertures having average EHD's of from about 7 mils to about 30 mils, and small sized apertures or holes, sometimes referred to as micro-sized holes, having average EHD's of from about 1 mil to about 7 mils. Such apertured films have an open area in the range of from about 3% to about 13%. It has been found that using orifice strips having orifices whose diameters range from about 10 to 25 mils results in the formation of apertures in the film having an average EHD of about 7 mils to about 17 mils. The fibrils surrounding and defining the micro-holes and the large sized holes are described in detail in co-pending patent application Ser. No. 08/417,404. The fibrils have lengths ranging from about 0.005 inch (0.013 cm) to about 0.05 inch (0.127 cm); widths ranging from about 0.001 inch (0.003 cm) to about 0.035 inch (0.089 cm); and thicknesses ranging from about 0.00025 inch (0.006 cm) to about 0.002 inch (0.005 cm). Photographs in FIGS. 12–18A, B show the combination of micro-holes and large sized holes of an apertured film made in accordance with the invention. Photographs in FIGS. 18C, D show large sized holes of an apertured film made in accordance with the invention.

The combination of large sized holes and micro-holes of the dimensions discussed above yield an improvement in the clean and dry properties of the film when used as a topsheet for a sanitary napkin. The resulting open area is in the range of 3 to 13%. In the prior art film having micro-holes only (see co-pending application Ser. No. 8/417,404 U.S. Pat. No. 5,567,376), when 5 mil diameter columnar jets of water are used, the resulting apertured film has micro-holes with an average EHD of 3 mils, and has an open area of about 3%. The increased aperture size and open area in an apertured film having large sized holes in combination with micro-holes in accordance with the invention provides an improved level of aperture size and open area so as to strike an advantageous balance: large enough apertures to rapidly accept a flow of menstrual fluid and to allow it to pass through to the napkin's absorbent core, but small enough to mask the stain on the absorbent pad to give the consumer the perception of cleanliness. Thus, the absorbent products of the present invention made with the apertured films of the present invention have much improved clean and dry properties.

In a preferred embodiment of the invention, the starting film is apertured by large diameter, low pressure columnar water jets and small diameter, high pressure columnar water jets. This combination of jets at both high and low pressure produces larger apertures and greater open area than films made with small diameter high pressure jets alone. Films made by this embodiment also appear softer to the user than films made only with large diameter, low pressure jets.

Figure 19:
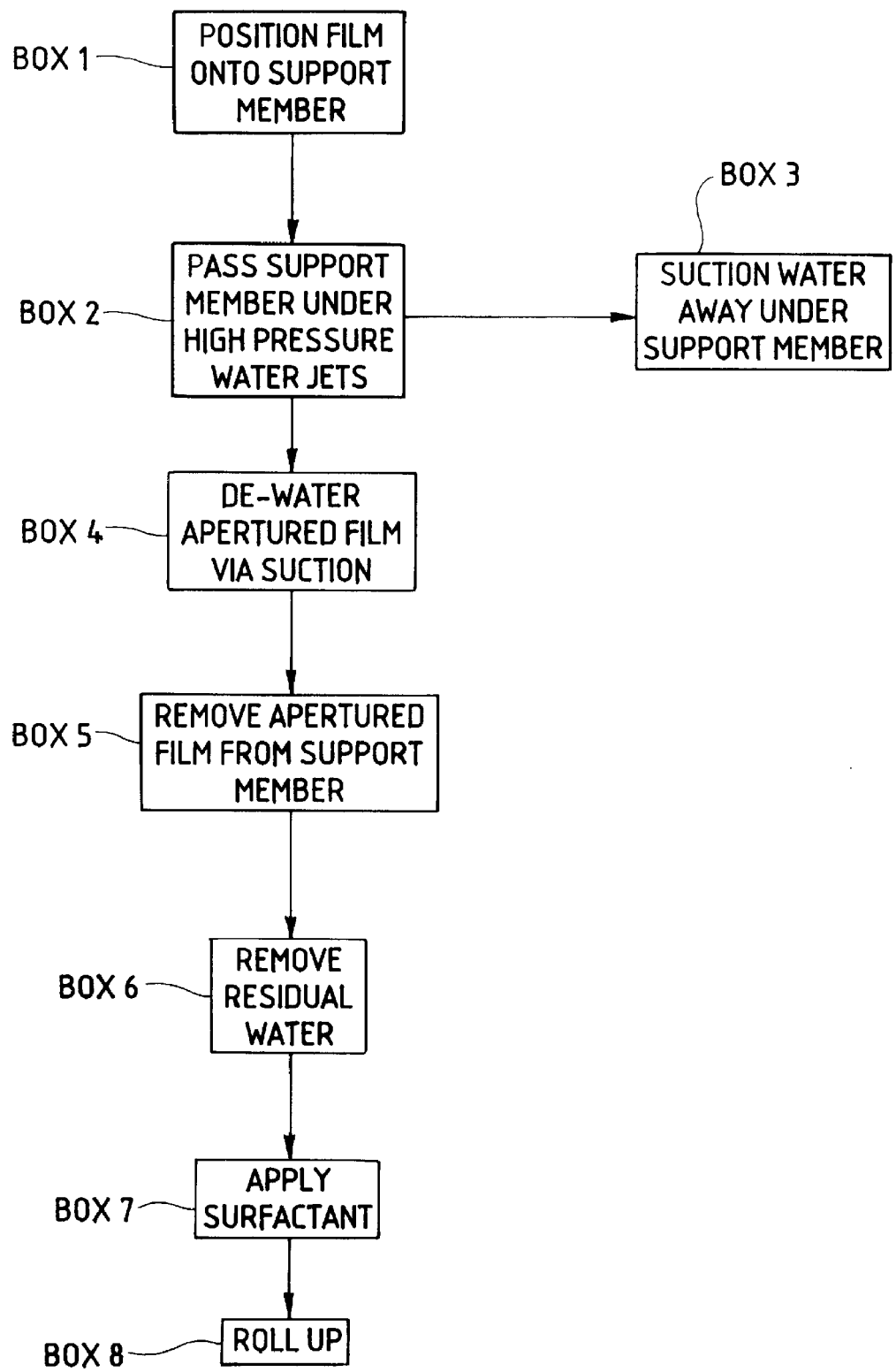
FIG. 19 is a block diagram showing the various steps of the process for producing the apertured film in accordance with the present invention.

FIG. 19 is a block diagram showing the several steps in the process for producing the novel apertured films of the present invention. The first step in the process is to position a piece of thin, stretchable film of thermoplastic polymer material on a backing or support member (Box 1). The support member with the stretchable film thereon is passed under high pressure fluid ejecting nozzles (Box 2). The preferred fluid is water. The water is transported away from the support member, preferably using a vacuum (Box 3). The film is de-watered, suction being preferred for this purpose (Box 4). The de-watered apertured film is removed from the support member (Box 5). Residual water is removed from the apertured film, e.g., by applying a stream of air thereto (Box 6). Surfactant is next applied to the apertured film (Box 7). The apertured film is then rolled up to await use as is or as a structural component of another product such as a sanitary napkin, disposable diaper or wound dressing (Box 8).

Figure 20:
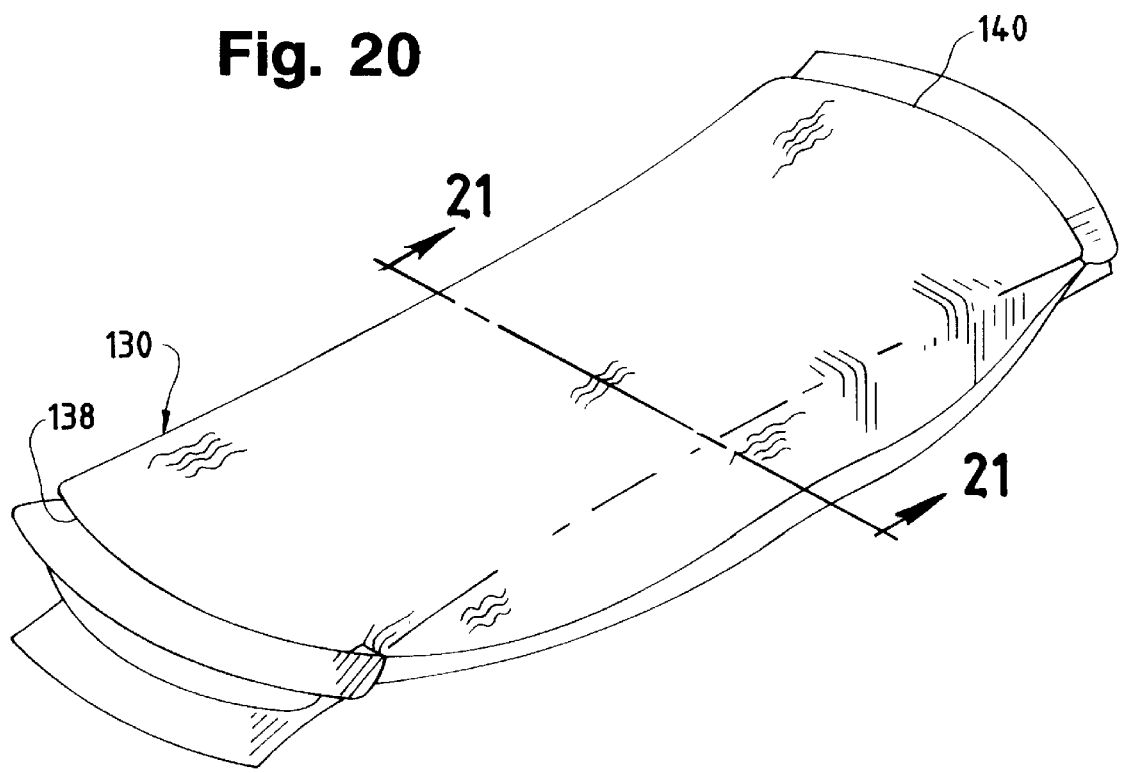
FIG. 20 is a perspective view of a sanitary napkin comprised of an apertured film according to the present invention.
Figure 21:
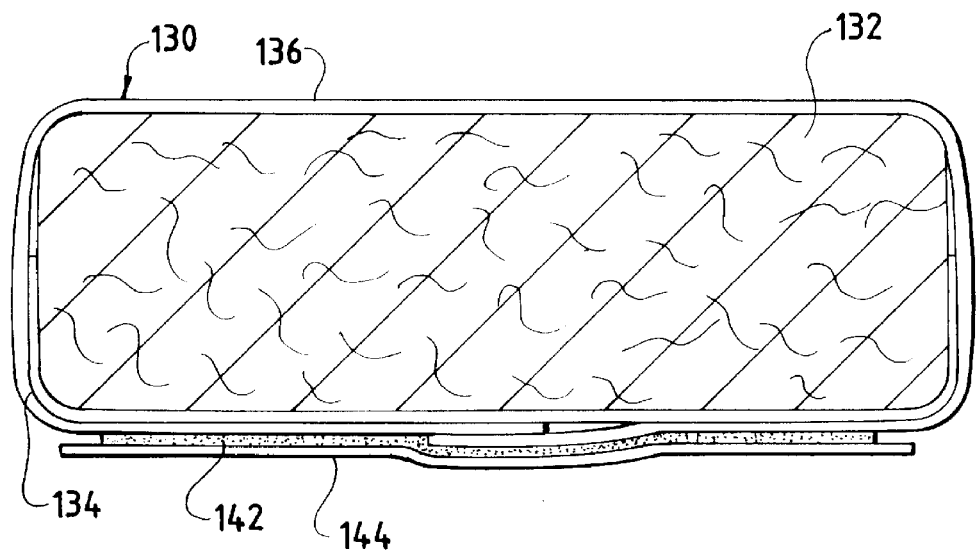
FIG. 21 is a view, partially in section, taken along line 21—21 of FIG. 20.

Referring to FIGS. 20 and 21, there is shown a sanitary napkin 130 comprising an absorbent core 132 of wood pulp fibers, a thin, fluid-impermeable barrier film 134 and a covering material 136 which may be any of the apertured films of the invention. Preferably, the covering film material has the structure shown and described herein. Barrier film 134, which may comprise, e.g., a thin film of polyethylene, contacts the lower surface of absorbent core 132 and runs part way up the longitudinal sides of the absorbent core. Covering material 136 has a length somewhat longer than the length of the absorbent core and is wrapped around the absorbent core and barrier film as shown in FIG. 21. The longitudinal edges of the cover material are overlapped and sealed together on the lower surface of the napkin in the usual manner. In the embodiment illustrated, the cover material is sealed to itself at the ends 138, 140 of the sanitary napkin. As illustrated in FIG. 21, sanitary napkin 130 has a layer of adhesive 142 for adhering the napkin to the undergarment of the user. Adhesive 142 is protected prior to use by a removable release strip 144.

EXAMPLE 1

In one embodiment of the apertured film in accordance with the invention, the starting material is an embossed film supplied by Exxon Chemical under the designation EMB-631, and having a thickness of 0.95 mils. This film is corona discharge treated on its male side. The film is placed on the forming member shown in FIGS. 8–10 which is mounted on a support drum as described in co-pending applications Ser. Nos. 08/417,404 U.S. Pat. No. 5,567,376 and 08/417,408 abandoned to Turi et al. with the corona-treated male side of the film facing away from the forming member. Two manifolds for directing columnar streams of water at the film were used. The first, or upstream, manifold has the orifice configuration shown in FIG. 7D of the drawings, i.e., there are two offset rows 92, 94 of orifices 92', 94', each of the orifices having a diameter of 0.025 inches. The orifices are spaced a distance of 0.038 inches center-to-center to provide a total of 52.6 holes per inch. The second, or downstream, manifold has the orifice configuration shown in FIG. 7A of the drawings, i.e., there is a single row of orifices each having a diameter of 0.005 inches. These orifices are spaced 0.020 inches on a center-to-center basis. There is a total of 50 such orifices per inch. Water having a temperature of 165° F. is supplied at a pressure of 165 psig to the first manifold, and at a pressure of 1400 psig to the second manifold. The film is passed under the manifolds at a speed of 435 feet per minute. The suction pressure inside the drum is minus 50 inches of water. The film is dewatered with the apparatus shown in FIG. 4 and is dried with the apparatus shown in FIG. 5. Following drying, the male side of the film is kiss-coated with a 48.8% solution of Tween-20 in water to a solution add-on of 0.25 mg/in$^2$. Subsequent rolling of the film effects transfer of the surfactant solution from the corona-treated male side to the female side. After the surfactant solution ultimately dries, the film has a bulk surfactant add-on (including all surfaces of the film) of 0.12 mg/in$^2$. The resulting apertured film has an air permeability of approximately 325 cubic feet per minute per square foot (cfm/ft$^2$) at a pressure differential ($\Delta P$) of 0.5 inches of water. The film has a measured open area of 6.24% and an average ECD of 10–11 mils. ECD (Equivalent Circular Diameter) is a calculated aperture diameter that is based on a measurement of the area of the aperture. The area is measured using the disclosed hardware and software for measuring EHD in co-pending patent application Ser. No. 08/417,404 now U.S. Pat. No. 5,561,376. The formula for ECD is ECD=$(4A/\pi)^{1/2}$ where A is the measured area of an aperture. There is an average of 500 apertures per square inch. The bulk thickness is 14.5 mils.

EXAMPLE 2

Another embodiment of the apertured film of the invention was made using the same starting film and forming member as used in Example 1. The line speed was 50 yds/min. Two manifolds for directing columnar streams of water at the film were used. The first, or upstream, manifold has the orifice configuration shown in FIG. 7C of the drawings, i.e., there are two offset rows 88, 90 of orifices 88', 90', each of the orifices having a diameter of 0.020 inches. The orifices are spaced a distance of 0.032 inches center-to-center to provide a total of 62.5 holes per inch. The second, or downstream, manifold has the orifice configuration shown in FIG. 7A of the drawings, i.e., there is a single row of orifices each having a diameter of 0.005 inches. These orifices are spaced 0.020 inches on a center-to-center basis. There is a total of 50 such orifices per inch. Water having a temperature of 160° F. is supplied at a pressure of 150 psig to the first manifold, and at a pressure of 1500 psig to the second manifold. The drum had a vacuum of 6 inches of Hg (−20.4 kPa).

In the dewatering section, there were six dewatering knives, and a vacuum of 4" of Hg. The air temperature for the first set of air knives was 180° F. The air temperature for the second set of air knives was 120° F. There were two film drying cylinders and each cylinder had five heated air knives. The hot air temperature for the knives was 150° F., and the vacuum was less than 1" of water.

The apertured film produced according to Example 2 was analyzed by microscopy. Open area, hole size distribution and total features (number of holes) were measured by image analysis techniques, with the following results:

| Open Area (mean) | St. Dev. | E.H.D.* (mean) | ECD (mean) | St. Dev. | Aperture Count |
|---|---|---|---|---|---|
| 6.19% | .68 | 7.61 mils | 10.85 mils | 10.47 mils | 858/sq.in. |

*EHD is measured as discussed in co-pending patent application Ser. No. 08/417,404 U.S. 5,567,376, which is incorporated by reference.

The characteristics of the orifice strips used in the experiments described below are shown in Table 1:

TABLE 1

Characteristics of Orifice Strips

| Orifice Strip ID | Orifice Size (inches) | Number Of Rows Of Orifices Per Orifice Strip | Intra-Row Spacing Between Orifices (center-to-center, in.) | Number Of Orifices Per Strip Per Inch Of Orifice Strip |
|---|---|---|---|---|
| a | 0.005 | 1 | 0.020 | 50 |
| b | 0.010 | 2 | 0.015 | 133 |
| c | 0.015 | 2 | 0.022 | 90.9 |
| d | 0.020 | 2 | 0.032 | 62.5 |
| e | 0.025 | 2 | 0.038 | 52.6 |
| f | 0.025 | 1 | 0.083 | 12 |

Experimentation With Batch Formation Of Films

The batch film aperturing apparatus used in the experiments reported in Table 2 below was similar to that shown in FIG. 3 of the drawings. However, only one water manifold 42 was used, and only one of the available vacuum slots was used. Each of the orifice strips labeled "b" through "f" in Table 1 was in turn mounted in the single water jet manifold and used to make one or more apertured films as shown in Table 2. The starting film and forming member were the same as those used in Example 1.

A piece of starting film was mounted to the outer surface of the forming member by a series of pins projecting from the forming member. The honeycomb support drum was rotated so that the mounted film was out of line with the single orifice strip. Vacuum was applied to the inside of the honeycomb support drum. Heated, pressurized water was supplied to the manifold. The honeycomb support drum motor was rotated to pass the starting film once under the orifice strip. The resultant film was removed from the forming member and air dried. Process conditions used to make films and the resultant film properties are shown in Table 2 below.

TABLE 2

Batch Film Aperturing Experiments

| Ex. # | Orifice ID | Water Pressure (psi) | Water Temp. (°F.) | Vacuum* (in. Water) | Film Speed (ft/min) | Open Area (%)** | Mean Equivalent Hydraulic Diameter (EHD)** (mils) |
|---|---|---|---|---|---|---|---|
| 1 | b | 350 | 160 | 60 | 150 | 3.6 | 10.7 |
| 2 | b | 550 | 160 | 60 | 150 | 6.5 | 10.3 |
| 3 | b | 1000 | 160 | 60 | 150 | 8.5 | 7.7 |
| 4 | c | 200 | 160 | 60 | 150 | 2.9 | 11.7 |
| 5 | c | 400 | 160 | 60 | 150 | 8.7 | 16.3 |
| 6 | c | 550 | 160 | 60 | 150 | 11.7 | 14.3 |
| 7 | c | 850 | 160 | 60 | 150 | 11.5 | 8.7 |
| 8 | d | 160 | 160 | 60 | 150 | 1.5 | 11.1 |
| 9 | d | 250 | 160 | 60 | 150 | 8.1 | 17.1 |
| 10 | d | 350 | 160 | 60 | 150 | 9.4 | 14.7 |
| 11 | d | 550 | 160 | 60 | 150 | 13.2 | 13.7 |
| 12 | e | 150 | 160 | 60 | 150 | 2.0 | 10.1 |
| 13 | e | 240 | 160 | 60 | 150 | 7.4 | 14.9 |
| 14 | e | 375 | 160 | 60 | 150 | 12.8 | 17.2 |
| 14a | f | 150 | 160 | 60 | 150 | 3.5 | 13.0 (1) |
| 14b | f | 200 | 160 | 60 | 150 | 5.71 | 12.8 (1) |
| 14c | f | 250 | 160 | 60 | 150 | 6.0 | 11.5 (1) |

*vacuum value is inches of water below atmospheric pressure.
**Open Area and EHD were measured according to the method disclosed in co-pending application Ser. No. 08/417,404, which is incorporated herein by reference.
(1) = ECD The data indicate the following trends:
Increasing the fluid pressure with an orifice strip of a given size increases open area.
Increasing the orifice diameter increases open area at a given fluid pressure.
Due to stretch of material that occurs during the process of forming apertures, the weight per area of the film is reduced to about 0.47 oz/sq.yd, which is 65% of the initial film weight per unit area. When the 0.025 inch diameter orifice strips spaced at 0.038 inch, 0.050 inch, 0.062 inch and 0.075 inch of Table 8 were used, the open area decreased from 13.1% to 12.0, 11.2, and 10.1% respectively.

Experimentation With Continuous Formation Of Film

Additional embodiments of films according to the present invention were made using the starting film, forming member and general procedure of Example 1. The characteristics of the orifice strips used are described in Table 1 above. All of the runs were made using water at 160° F., with the corona treated male side of the starting film facing away from the forming member. The number of orifice strips used, and their characteristics and processing conditions are shown in the following table:

TABLE 3

Continuous Film Aperturing Experiments

| Experiment # | Orifice Strip #1 | | Orifice Strip #2 | | Orifice Strip #3 | | Line |
|---|---|---|---|---|---|---|---|
| | Orifice Strip ID | Pressure (psi) | Orifice Strip ID | Pressure (psi) | Orifice Strip ID | Pressure (psi) | Speed (ft/min) |
| 15 | d | 150 | | | | | 120 |
| 16 | d | 150 | a | 1000 | | | 120 |
| 17 | d | 150 | a | 1000 | a | 1000 | 120 |
| 18 | a | 1000 | | | | | 120 |
| 19 | a | 1000 | a | 1000 | | | 120 |
| 20 | a | 875 | a | 875 | a | 875 | 120 |
| 21 | a | 875 | a | 875 | a | 875 | 150 |
| 22 | a | 1000 | d | 150 | | | 120 |
| 23 | a | 1000 | d | 150 | a | 1000 | 120 |

Following air drying, the films were kiss-coated with an aqueous solution of Tween 20 surfactant at a concentration of 48.8% on the corona-treated male side to produce a bulk surfactant add-on of 0.12 mg/in$^2$ of film as described hereinabove in connection with Example 1.

The apertured films produced in these experiments were evaluated for air permeability, aperture size, open area, strikethrough and bending length (a measure of film stiffness). Tests were run according to the following methods well known in the art. Air permeability was tested according to ASTM D737. Film aperture size and open area were determined and used to calculate Equivalent Circular Diameter (ECD). Strikethrough is a measurement of the time required for 5 cc of a test fluid to be absorbed through the film supported on ground fluff wood pulp. The test fluid is a mixture of 75% by weight of defibrinated bovine blood and 25% by weight of a 10% by weight aqueous solution polyvinylpyrrolidone (GAF Povidone K-90). Bending length in the machine direction (MD) and cross direction (CD) were measured according to ASTM D1388. The properties of the film produced in continuous runs are shown in Tables 4–7 below.

TABLE 4

Continuous Apertured Film Properties - Air Permeability

| Experiment # | Air Permeability CFM/SQFT @ 0.5 in. H$_2$O ΔP |
|---|---|
| 15 | 139.33 |
| 16 | 222.00 |
| 17 | 246.67 |
| 18 | 107.00 |
| 19 | 143.67 |
| 20 | 173.67 |
| 21 | 170.67 |
| 22 | 214.33 |
| 23 | 212.67 |

The data in Table 4 show that the combination of large diameter and small diameter orifices (experiments 16, 17, 22 and 23) produces a more permeable, open film than films made with small diameter orifices alone (experiments 18–21). It is believed that the use of large diameter orifices, albeit used at lower water pressure, is the primary cause for the creation of large holes. Further, it is believed that the use of smaller diameter orifices is the primary cause for the creation of the smaller micro-holes.

TABLE 5

Continuous Apertured Film Properties - Aperture Size And Open Area

| Experiment # | Average Equivalent Circular Diameter (mils) | EC Standard Deviation (mils) | Open Area (%) | No. Of Apertures/square inch |
|---|---|---|---|---|
| 15 | 16.46 | 10.12 | 4.55 | 197 |
| 16 | 8.62 | 9.22 | 5.34 | 515 |
| 17 | 7.48 | 8.47 | 5.34 | 715 |
| 18 | 4.65 | 2.66 | 2.31 | 1125 |
| 19 | 4.53 | 2.65 | 2.48 | 1283 |
| 20 | 4.00 | 2.25 | 2.38 | 1635 |
| 21 | 4.16 | 2.48 | 2.53 | 1519 |
| 22 | 6.49 | 5.59 | 4.15 | 806 |
| 23 | 6.88 | 6.18 | 4.88 | 856 |

The data in Table 5 show that the combination of large diameter and small diameter orifices (experiments 16, 17, 22, and 23) produce a film with larger aperture size and increased open area than films made with small diameter orifices alone (experiments 18–21).

Figure 22:
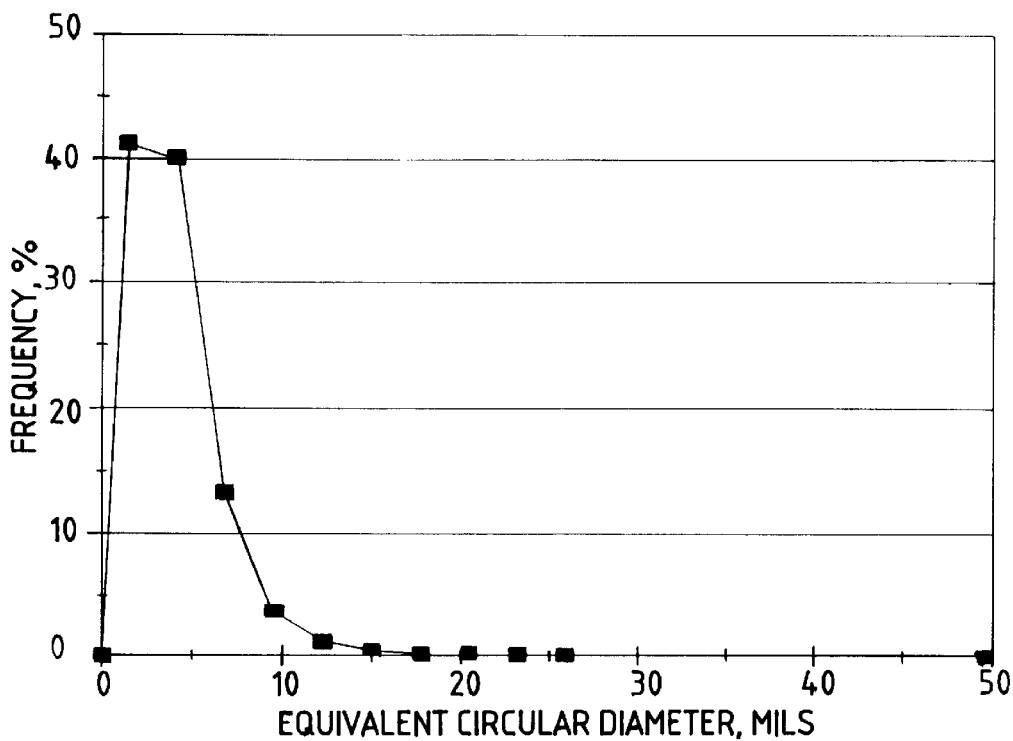
FIG. 22 is a graph depicting aperture size distribution in a sample of apertured film made at 875 psig. on an apparatus using three orifice strips each having a plurality of orifices, all of the orifices being 5 mils in diameter.
Figure 23:
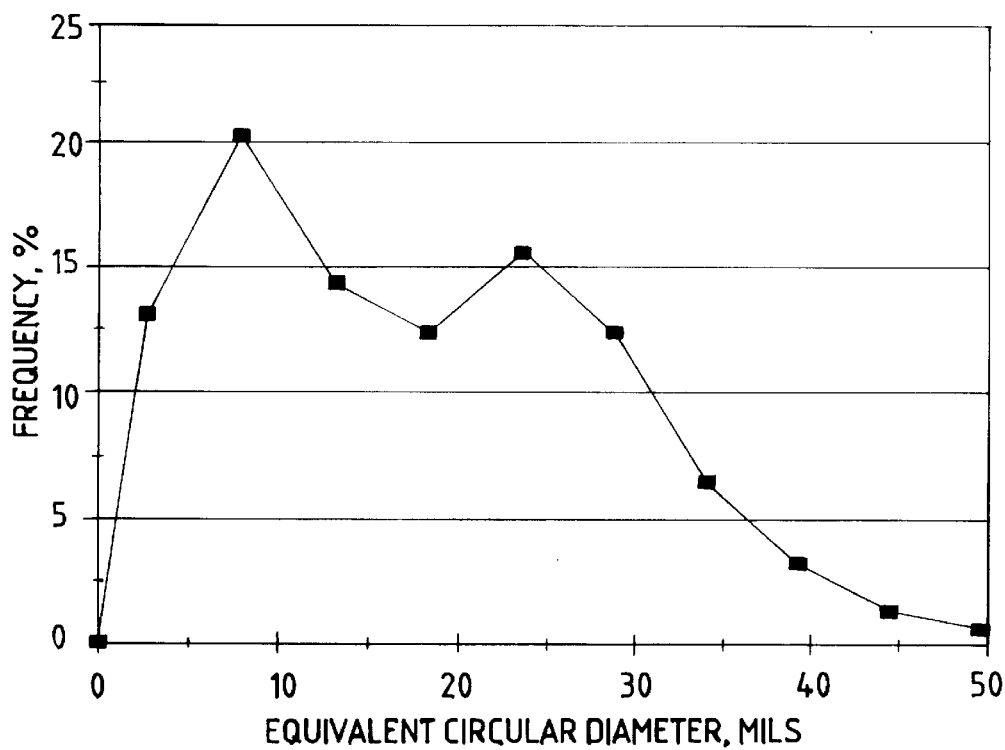
FIG. 23 is a graph depicting aperture size distribution in a sample of apertured film made on an apparatus comprising a single orifice strip having a plurality of orifices each 20 mils in diameter, said orifice strip being shown in FIG. 7C.
Figure 24:
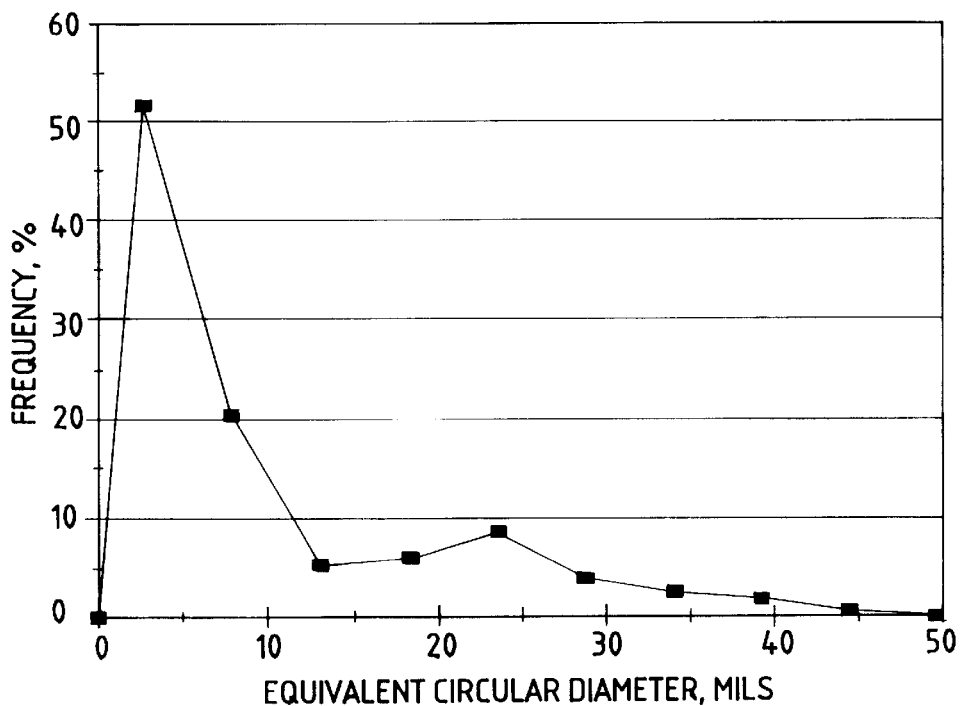
FIG. 24 is a graph depicting aperture size distribution in a sample of apertured film made on an apparatus comprising a first orifice strip (shown in FIG. 7C) having a plurality of orifices, all of which have a diameter of 20 mils, and a second orifice strip, downstream of the first strip, wherein the second strip (shown in FIG. 7A) has a plurality of orifices all of which have a diameter of 5 mils.
Figure 25:
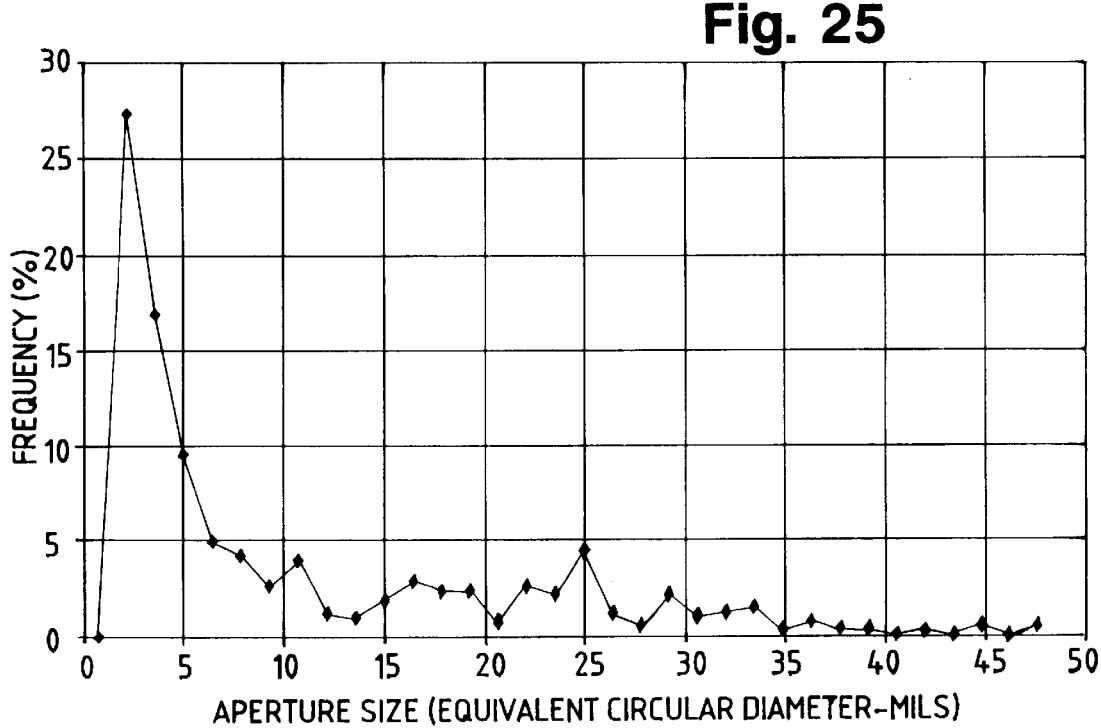
FIG. 25 is a graph depicting aperture size distribution in a sample of apertured film made in accordance with the invention.

FIGS. 22, 23 and 24 are graphs that show the aperture size distribution of films produced in these experiments with a 5 mil diameter orifice strip (Experiment No. 20), a 20 mil diameter orifice strip (Experiment No. 15), and the combination of a 20 mil orifice strip followed by a 5 mil orifice strip (Experiment No. 16), respectively (see Table 3 above). As seen from these graphs, the apertured films produced with orifice strips of different diameters have aperture sizes that reflect the effects of various of the individual orifice diameters. The film (Experiment No. 20) produced with only a 5 mil orifice strip has apertures most of which have a diameter under 10 mils (see FIG. 22). The film (Experiment No. 15) produced by a 20 mil orifice strip only has a broader distribution of aperture diameters, with peak concentrations at approximately 9 mils and at approximately 23 mils (see FIG. 23). The film (Experiment No. 16) produced by a combination of a 5 mil orifice strip and a 20 mil orifice strip has a distribution of hole diameters that is primarily concentrated under 12 mils, and has slight concentration of holes with a diameter of around 23 mils (see FIG. 24). These three graphs indicate that the 5 mil orifices create microholes primarily, that the 20 mil orifices create larger sized holes primarily, and that a combination of 5 mil orifices and 20 mil orifices creates a combination of micro-holes and large sized holes. Comparable data is shown in FIG. 25 which shows aperture size distribution in a sample of apertured film having micro-holes and large-sized holes in accordance with the invention that was made on a commercial production line.

TABLE 6

Continuous Apertured Film Properties - Strikethrough Time

| Experiment # | Strikethrough Time (sec) |
|---|---|
| 15 | 16.3 |
| 16 | 17.6 |
| 17 | 13.5 |
| 18 | 28.8 |
| 19 | 25.6 |
| 20 | 20.2 |
| 21 | 22.9 |
| 22 | 15.8 |
| 23 | 17.10 |

The data in Table 6 show that either large diameter orifices alone, or the combination of large diameter and small diameter orifices (experiments 15, 16, 17, 22 and 23) produce a film with faster strikethrough times than films made with small diameter orifices alone (experiments 18–21).

TABLE 7

Continuous Apertured Film Properties - Film Stiffness

| Experiment # | MD Bending Length (mm) | CD Bending Length (mm) |
|---|---|---|
| 15 | 22.8 | 6 |
| 16 | 26.3 | 6.5 |
| 17 | 22.3 | 6.5 |
| 18 | 27 | 6.3 |
| 19 | 26.8 | 5.5 |
| 20 | 26 | 9.5 |
| 21 | 25.5 | 8.5 |
| 22 | 23.5 | 5.8 |
| 23 | 27.30 | 8.0 |
| comparable commercial product | 21.8 | 14.8 |

The data indicate that the MD bending length of the films of experiments 15–23 is comparable to those of other commercial sanitary napkin plastic covers, and that the CD bending length of the films is lower than comparable commercial films. Hence, stiffness and expected comfort of the films of the present invention are expected to be comparable or superior to that of other commercial apertured films.

Figure 26:
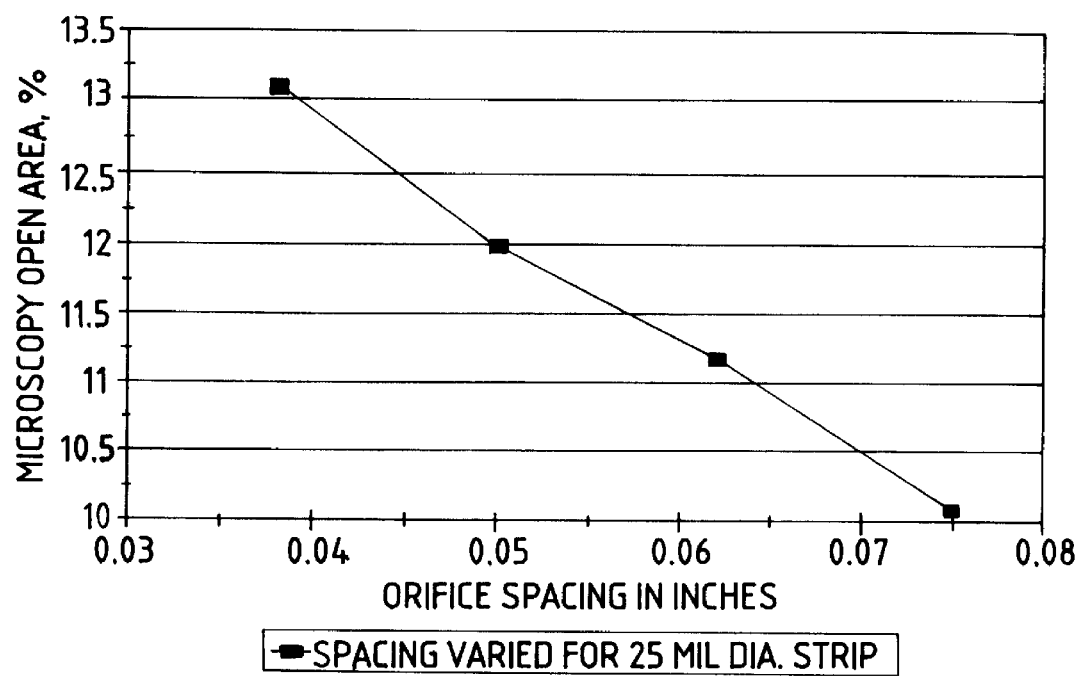
FIG. 26 is a graph depicting the results of comparison in which the spacing of the orifices comprising the orifice strip is varied.

Results of additional experimentation are shown in FIG. 26. In these experiments, the spacing of the orifices was varied to determine the effect on film open area. Two water jet manifolds were used in these experiments. The first, or upstream, manifold had one orifice strip with two rows of orifices on respective sides of the longitudinal center line of the strip, the two rows of orifices being offset as shown in FIGS. 7B–7D, i.e., the offset distance was one-half the intra-row, center-to-center spacing of the orifices. All orifices had a diameter of 0.025 inch. The center-to-center spacing of the orifices for each experiment was varied as reported in Table 8.

The second, or downstream, manifold had one orifice strip with a single row of orifices therein. The orifices each had a diameter of 0.005 inch and were spaced 0.020 inch on a center-to-center basis. Water was supplied to the first manifold at 150 psig. Water was supplied to the second manifold at 1000 psig. The film traveled at 150 ft/min. The drum vacuum was 60 inches water. The following Table 8 indicates the open area, number of apertures per $in^2$, ECD and air permeability for the resulting apertured films.

TABLE 8

| Film Number | Large Orifice* Spacing, inch | Open Area, % | Number of Apertures | Equivalent Circular Diameter, inch | Air Permeability |
|---|---|---|---|---|---|
| 24 | 0.038 | 13.1 | 914 | 0.0099 | 505 |
| 25 | 0.050 | 12.0 | 1136 | 0.0085 | 476 |
| 26 | 0.062 | 11.2 | 1151 | 0.0081 | 465 |
| 27 | 0.075 | 10.1 | 1299 | 0.0072 | 435 |

*Two rows of 25 mil diameter orifices.

Air permeability was measured per ASTM D737; results are reported in Table 8 in cubic feet per minute per square foot of film. The air permeabilities of film apertured at 150 psig and 150 ft/min. were 310 cfm/sf for the 25-mil diameter orifice strip (only) (0.038 inch spacing) control, which decreased nearly linearly to 245 cfm/sf for the 0.075 inch spacing. When the 5-mil diameter strip was added, the air permeability increased to 505 cfm/sf for the control spacing. There was a nearly linear decrease with spacing to a value to 435 cfm/sf at 0.075 inches. At 150 ft/min., the combination of the large diameter, 25 mil diameter control strip with the 5-mil strip provides about 195 cfm/sf beyond the measured air permeability of the large hole strip alone. The above data indicates that as large orifice spacing increases, fewer large-sized holes are produced, and the open area is accordingly reduced.

Apertured films made according to co-pending Ser. No. 08/417,404 and films of the present invention were tested and compared. The films were prepared on the continuous production line under the following conditions shown in Table 9.

TABLE 9

Apertured Film Preparation And Properties

| Film made according to Precursor Film | Ser. No. 08/417,404 Exxon EMB-631 | Present Invention Exxon EMB-631 |
|---|---|---|
| Forming Member Pattern | sinusoidal (12 rails/in.) | sinusoidal (12 rails/in.) |
| Number of Orifice Strips | 3 | 2 |
| Orifice Strip # 1 Pressure (psig) | 875 | 150 |
| Orifice Strip # 2 Pressure (psig) | 875 | 1000 |
| Orifice Strip # 3 Pressure (psig) | 875 | |
| Orifice ID | a/a/a | d/a |
| Orifice size (mils) | 5/5/5 | 20/5 |
| Water Temperature | 158° F. | 160° F. |
| Line Speed (ft./min.) | 150 | 150 |
| Surfactant Treatment | Tween 20 | Tween 20 |

Sanitary napkins comprising a cover, an absorbent core and a backsheet were prepared using the apertured films of Table 10 as coverstock materials. Two different napkin designs were constructed and tested for strikethrough and rewet using synthetic menstrual fluid. Synthetic menstrual fluid was prepared dissolving 0.15% polyacrylamide in isotonic phosphate buffer. Approximately 0.3% Germaben was added to prevent bacterial growth. The pH of the solution was measured as 7.4, and the viscosity at 30 centipoise at one radian per second. Results are shown in Tables 11 and 12 below.

TABLE 10

Strikethrough And Rewet Of Napkins Made With Apertured Films Napkin Design #1

| Film made according to | Ser. No. 08/417,404 | Present Invention |
|---|---|---|
| 5 cc strikethrough time (sec) | 68 | 62 |
| Rewet (g) | 0.04 | 0.02 |

TABLE 11

Strikethrough And Rewet Of Napkins Made With Apertured Films Napkin Design #2

| Film made according to | Ser. No. 08/417,404 | Present Invention |
|---|---|---|
| 5 cc strikethrough time (sec) | 39 | 39 |
| Rewet (g) | 0.11 | 0.05 |

The data in Table 10 and Table 11 show strikethrough time and rewet absorption. The strikethrough time refers to the time elapsed for absorption of 5 cc of synthetic menstrual fluid, with a lower time being desirable. Rewet absorption refers to the amount of fluid that can be absorbed in a filter paper that is placed in contact with a sanitary napkin that has absorbed 5 cc of fluid in the strikethrough test, with a lower amount of rewet being desirable.

The data demonstrate that the larger open area and aperture size of the films of the present invention give rise to at least equal or faster strikethrough times than the prior art films. However, even though the improved films of the present invention have larger open area and larger average aperture size than the prior art films, the napkins made with the films of the present invention have unexpectedly lower rewet values relative to prior art films.

Another test used to measure the rate of transport of menstrual fluid through the apertured film is the "Drop Test". Comparative data for the films of the present invention versus prior art films are shown in Table 12 below.

TABLE 12

Drop Test Data For Apertured Films On Napkin Design #1

| Film Made According To | Ser. No. 08/417,404 | Present Invention |
|---|---|---|
| Absorption Time (sec) (0°) | 27 | 8 |
| Absorption Time (sec) (45° transverse tilt) | Drop rolled off | 17 |

The data in Table 12 refers to the time required for absorption of a drop of synthetic menstrual fluid, with a lower time being desirable. In the first test, the film was level. In the second test, the film was tilted to an angle of 45°. The data further illustrate the superior fluid transport properties of films of the present invention relative to prior art films.

Apertured plastic films made according to the present invention exhibit the following characteristics: tactile softness; textile-like look and feel; low film stiffness as described in Table 7; aperturing patterns, open areas, and pore sizes ranges as described in Table 5 and FIGS. 23–26; low basis weight ($\leq 0.7$ oz/yd$^2$); and film/air/synthetic menstrual fluid contact angles on both sides of the film of $\leq 70°$.

The apertured film of the present invention, with surfactant treatment, offers overall comparable fluid penetration rate (as measured by 5 cc synthetic menstrual fluid strikethrough times—test method described in co-pending patent application Ser. No. 08/417,404 U.S. Pat. No. 5,567,376 ), which is improved over non-surfactant-treated films by approximately 34% in either a pulp absorbent core construction or a peat moss based absorbent construction.

What is claimed is:

1. A method for forming an apertured film from a stretchable thermoplastic polymeric material comprising:
   a) providing a starting film comprising said stretchable thermoplastic polymeric material having an upper surface and a lower surface;
   b) providing a backing member comprising localized support regions for supporting said starting film, recessed zones into which the film may be deformed by the application thereto of fluid forces; and means for allowing said applied fluid to be transported away from said backing member;
   c) supporting said starting film on said backing member with portions of the lower surface of said film being in contact with the support regions of said backing member and with the upper surface of said film facing away from said backing member;
   d) forming irregular size micro-holes and large sized holes in said starting film by directing a fluid in the form of substantially non-diverging, columnar streams from at least two sets of orifices against the upper surface of said starting film in a zone of contact to cause said starting film to stretch between said backing member localized support regions over said recessed zones, the orifices of the first set having a diameter greater than ten mils and the fluid supplied thereto having a pressure less than 500 psig. to cause said starting film to rupture into a multiplicity of said large sized holes in said starting film between said localized support regions, the orifices of the second set having a diameter less than or equal to ten mils and the fluid supplied thereto having a pressure of at least 500 psig., to cause said starting film to rupture into a multiplicity of said micro-holes in said starting film between said localized support regions;
   e) moving said film from said contact zone; and
   f) removing said now-apertured film from said backing member.

2. A method of forming an apertured film from a stretchable thermoplastic polymeric material in accordance with claim 1 wherein said first set of orifices have a diameter in the range of about 10 mil to about 30 mils.

3. A method of forming an apertured film from a stretchable thermoplastic polymeric material in accordance with claim 1 wherein said second set of orifices have a diameter in the range of about 1 mils to about 10 mils.

4. A method of forming an apertured film from a stretchable thermoplastic polymeric material in accordance with claim 1 wherein said first set of orifices have a diameter in the range of about 15 mils to about 35 mils.

5. A method of forming an apertured film from a stretchable thermoplastic polymeric material in accordance with claim 1 wherein said second set of orifices have a diameter in the range of about 3 mils to about 7 mils.

6. A method of forming an apertured film from a stretchable thermoplastic polymeric material in accordance with claim 1 wherein said fluid emitted from said first set of orifices has a pressure in the range of about 100 psig to about 500 psig.

7. A method of forming an apertured film from a stretchable thermoplastic polymeric material in accordance with claim 1 wherein said fluid emitted from said second set of orifices has a pressure in the range of about 500 psig to about 2000 psig.

8. A method of forming an apertured film from a stretchable thermoplastic polymeric material in accordance with claim 1 wherein said fluid emitted from said first set of orifices has a pressure in the range of about 125 psig to about 200 psig.

9. A method of forming an apertured film from a stretchable thermoplastic polymeric material in accordance with claim 1 wherein said fluid emitted from said second set of orifices has a pressure in the range of about 800 psig to about 1500 psig.

10. A method of forming an apertured film from a stretchable thermoplastic polymeric material in accordance with claim 1 including the further step of providing a third set of orifices, said third set of orifices having a diameter less than or equal to about ten mils, the fluid supplied thereto having a pressure of at least 500 psig.

11. A method of forming an apertured film from a stretchable thermoplastic polymeric material in accordance with claim 10 wherein said third set of orifices have a diameter in the range of about 1 mils to about 10 mils.

12. A method of forming an apertured film from a stretchable thermoplastic polymeric material in accordance with claim 10 wherein said third set of orifices have a diameter in the range of about 3 mils to about 7 mils.

13. A method of forming an apertured film from a stretchable thermoplastic polymeric material in accordance with claim 10 wherein said fluid supplied to said third set of orifices has a pressure in the range of about 500 psig to about 3000 psig.

14. A method of forming an apertured film from a stretchable thermoplastic polymeric material in accordance with claim 10 wherein said fluid emitted from said third set of orifices has a pressure in the range of about 800 psig to about 1500 psig.

15. A method of forming an apertured film from a stretchable thermoplastic polymeric material in accordance with claim 1 wherein said micro-holes have an average EHD of about 1 mil to about 7 mils.

16. A method of forming an apertured film from a stretchable thermoplastic polymeric material in accordance with claim 1 wherein said micro-holes have an average EHD of about 2 mils to about 5 mils.

17. A method of forming an apertured film from a stretchable thermoplastic polymeric material in accordance with claim 1 wherein said large sized holes have an average EHD of about 7 mils to about 30 mils.

18. A method of forming an apertured film from a stretchable thermoplastic polymeric material in accordance with claim 1 wherein the fluid from the first set of orifices is directed against the upper surface of said starting film prior to directing the fluid from the second set of orifices.

19. A method of forming an apertured film from a stretchable thermoplastic polymeric material in accordance with claim 1 wherein said micro-holes are defined by fibrils.

20. A method of forming an apertured film from a stretchable thermoplastic polymeric material in accordance with claim 1 wherein said large sized holes are defined by fibrils.

21. A method for forming an apertured film from a stretchable thermoplastic polymeric material comprising:
  a) providing a starting film comprising said stretchable thermoplastic polymeric material and having an upper surface and a lower surface;
  b) providing a backing member comprising localized support regions for supporting said starting film, recessed zones into which the film may be deformed by the application thereto of fluid forces, and means for allowing said applied fluid to be transported away from said backing member,
  c) a supporting said starting film on said backing member with portions of the lower surface of said film being in contact with the support regions of said backing member and with the upper surface of said film facing away from said backing member;
  d) forming irregular large sized holes in said starting film by directing a fluid in the form of substantially non-diverging, columnar streams from a first set of orifices against the upper surface of said starting film in a zone of contact to cause said starting film to stretch between said backing member localized support regions over said recessed zones, said orifices in said first set having a diameter greater than or equal to ten mils and the fluid supplied thereto causing said starting film to rupture into a multiplicity of said large sized holes in said starting film between said localized support regions;
    forming irregular size micro-holes in said starting film by directing a fluid in the form of substantially non-diverging, columnar streams from a second set of orifices against the upper surface of said starting film in a zone of contact to cause said starting film to stretch between said backing member localized support regions over said recessed zones, said orifices in said second set having a diameter less than or equal to ten mils and the fluid emitted therefrom causing said starting film to rupture into a multiplicity of said micro-holes in said starting film between said localized support regions, said micro-holes being defined by fibrils of said thermoplastic material;
  e) moving said film from said contact zone; and
  f) removing said now-apertured film from said backing member.

22. A method for forming an apertured film from a stretchable thermoplastic polymeric material comprising:
  a) providing an embossed starting film comprising said stretchable thermoplastic polymeric material having an upper surface and a lower surface;
  b) providing a backing member comprising localized support regions for supporting said starting film, recessed zones into which the film may be deformed by the application thereto of fluid forces; and means for allowing said applied fluid to be transported away from said backing member;
  c) supporting said starting film on said backing member with portions of the lower surface of said film being in contact with the support regions of said backing member and with the upper surface of said film facing away from said backing member;
  d) forming irregular size micro-holes and large sized holes in said starting film by directing a fluid in the form of substantially non-diverging, columnar streams from at least two sets of orifices against the upper surface of said starting film in a zone of contact to cause said starting film to stretch between said backing member localized support regions over said recessed zones, the orifices of the first set having a diameter greater than ten mils and the fluid supplied thereto having a pressure less than 500 psig. to cause said starting film to rupture into a multiplicity of said large sized holes in said starting film between said localized support regions, the orifices of the second set having a diameter less than or equal to ten mils and the fluid supplied thereto having a pressure of at least 500 psig., to cause said starting film to rupture into a multiplicity of said micro-holes in said starting film between said localized support regions;

e) moving said film from said contact zone; and f) removing said now-apertured film from said backing member.

23. A method of forming an apertured film in accordance with claim 22, including providing said embossed starting film with corona discharge treatment on one side thereof.

24. A method of forming an apertured film in accordance with claim 22 including applying a surface active agent to one side of said apertured film.

* * * * *